(12) United States Patent
Leithem et al.

(10) Patent No.: US 8,497,410 B2
(45) Date of Patent: *Jul. 30, 2013

(54) METHOD FOR MAKING ABSORBENT PRODUCTS

(75) Inventors: Phyllis Leithem, McCleary, WA (US); Charles A. Kremers, Morrisville, PA (US); W. Paul Harrell, Fernandina Beach, FL (US); Stephen Lewis, Shelton, WA (US); Karl D. Sears, Shelton, WA (US); Quan He, Lacey, WA (US); Peter R. Abitz, Olympia, WA (US)

(73) Assignee: Rayonier TRS Holdings Inc., Jacksonville, FL (US)

( * ) Notice: Subject to any disclaimer, the term of this patent is extended or adjusted under 35 U.S.C. 154(b) by 336 days.

This patent is subject to a terminal disclaimer.

(21) Appl. No.: 12/932,198

(22) Filed: Feb. 18, 2011

(65) Prior Publication Data

US 2011/0209839 A1    Sep. 1, 2011

Related U.S. Application Data

(63) Continuation of application No. 09/334,125, filed on Jun. 15, 1999, now Pat. No. 7,919,667, which is a continuation of application No. 08/370,571, filed on Jan. 18, 1995, now abandoned, which is a continuation-in-part of application No. 08/184,377, filed on Jan. 21, 1994, now abandoned.

(51) Int. Cl.
*A61F 13/15* (2006.01)
*D21C 9/00* (2006.01)
*D21H 13/00* (2006.01)

(52) U.S. Cl.
USPC ............. 604/367; 604/368; 604/374; 162/90; 162/157.6

(58) Field of Classification Search
USPC .................... 604/367, 368, 374, 380; 162/90, 162/9, 70, 182, 78, 157.6
See application file for complete search history.

(56) References Cited

U.S. PATENT DOCUMENTS

| | | |
|---|---|---|
| 1,310,694 A | 7/1919 | Edwardes |
| 1,830,131 A | 11/1931 | Plumstead |
| 1,913,283 A | 6/1933 | McCormick |
| 2,083,575 A | 6/1937 | Novak |
| 2,683,088 A | 7/1954 | Reynolds |
| 2,880,726 A | 4/1959 | Stieg |
| 3,057,037 A | 10/1962 | Carney et al. |
| 3,105,491 A | 10/1963 | Harwood |
| 3,658,064 A | 4/1972 | Pociluyko |
| 3,658,613 A | 4/1972 | Steiger |
| 3,661,154 A | 5/1972 | Torr |
| 3,670,731 A | 6/1972 | Harmon |
| 3,739,782 A | 6/1973 | Bernardin |
| 3,809,604 A | 5/1974 | Estes |
| 3,897,782 A | 8/1975 | Tunc |
| 3,932,209 A | 1/1976 | Chatterjee |
| 4,081,316 A | 3/1978 | Aberg et al. |
| 4,096,289 A | 6/1978 | Nischwitz et al. |
| 4,103,062 A | 7/1978 | Aberson et al. |
| 4,104,214 A | 8/1978 | Meierhoefer |
| 4,105,033 A | 8/1978 | Chatterjee et al. |

(Continued)

*Primary Examiner* — Jacqueline F. Stephens
(74) *Attorney, Agent, or Firm* — Lucas & Mercanti, LLP

(57) ABSTRACT

A method of making personal hygiene articles of high absorbency from cellulosic fiber pulp without chemical cross-linking of the cellulosic fibers is disclosed. The method comprises interposing a sublayer of mechanically fluffed alkali extracted cellulosic fiber pulp between a fluid permeable layer and a fluid impermeable layer.

19 Claims, 2 Drawing Sheets

U.S. PATENT DOCUMENTS

| | | |
|---|---|---|
| 4,165,743 A | 8/1979 | Denning |
| 4,242,242 A | 12/1980 | Allen |
| 4,340,556 A | 7/1982 | Ciencewicki |
| 4,444,830 A | 4/1984 | Erickson |
| 4,689,118 A | 8/1987 | Makoui et al. |
| 4,767,848 A | 8/1988 | Makoui et al. |
| 4,888,093 A | 12/1989 | Dean et al. |
| 4,898,642 A | 2/1990 | Moore et al. |
| 4,911,700 A | 3/1990 | Makoui et al. |
| 4,919,681 A | 4/1990 | Tyler et al. |
| 5,019,063 A | 5/1991 | Marsan et al. |
| 5,071,681 A | 12/1991 | Manning et al. |
| 5,091,240 A | 2/1992 | Kajander et al. |
| 5,147,343 A | 9/1992 | Kellenberger |
| 5,413,747 A | 5/1995 | Akers et al. |
| 5,478,335 A | 12/1995 | Colbert |
| 5,766,159 A | 6/1998 | Martin et al. |
| 6,063,982 A | 5/2000 | Martin et al. |

METHOD FOR MAKING ABSORBENT PRODUCTS

CROSS REFERENCE TO RELATED APPLICATIONS

This application is a continuation of U.S. Ser. No. 09/334,125, filed Jun. 15, 1999 now U.S. Pat. No. 7,919,667, which is a continuation of U.S. Ser. No. 08/370,571, filed Jan. 18, 1995, now abandoned, which is a continuation-in-part of U.S. Ser. No. 08/184,377, filed Jan. 21, 1994, now abandoned.

This invention relates to pulps for absorbent products, more particularly this invention relates to novel use of modified pulps for absorbent products of household and hygienic uses such as diapers, incontinence and catamenial devices and the like and a method for preparing pulps of outstanding absorbency characteristics.

More particularly, this invention relates to the novel use of known technology—cold alkali extraction—to produce cellulosic pulps having altered and novel fiber properties desirable for end-use applications for absorbent and fluff pulp products.

Further, this invention relates to the production of the altered and novel pulps without addition of chemical additives such as sheet debonders. Still further this invention relates to the production of pulps having novel, desirable properties achieved without chemical modification steps such as cross-linking with chemical cross-linking agents.

Moreover, this invention relates to a novel use of a pulp product characterized and defined by its properties for suitable end uses of these pulps. Accordingly, novel pulp products can be obtained at reduced cost for the respective, economic effectiveness of these pulps when compared to pulps prepared by the prior art and suitable for the same purpose.

BACKGROUND FOR THE INVENTION

With the increasing prominence of disposable items, such as diapers, paper towels and the like, and in view of the widely prevalent use of absorbent tissues of various kinds, it has become important to obtain pulps of high absorbency, especially pulps that display high absorbency upon multiple rewetting.

Typically pulps that are used for hygienic absorption purposes such as baby diapers and the like are constructed with an outside "acquisition" layer, which is a layer of pulp of good bulking properties and good absorbency due to relative fiber stiffness. A bulky material will contain a high percentage of void spaces or pores. For an absorbent product, these pores are used to acquire, transport and store fluid. Longer, stiffer fibers make bulker air laid webs with more pore volume. Fluids are more easily acquired and transported if pore volume or bulk is high. The "acquisition" layer is positioned between the baby's skin and the absorbent core of the diaper. An "acquisition" layer of proper characteristics and properties allows the liquid to pass quickly into the absorbent core upon repeated wettings and at the same time this layer transmits the liquid into the principal absorbent core that holds the liquid. In a similar manner, an incontinent or catamenial device may be constructed. Further, wound dressing material may be construed in a like manner. These devices are absorbency products which require pulps having intensive absorbency properties.

Still further, absorbent multi-ply papers such as household towels may be constructed of multiple layers or plies including a core layer and thus these plies may be tailored according to the use to which these goods are being subjected or for the purpose these are employed.

Products such as diapers when used with an outside "acquisition" layer and an interior principal absorbent core, are presently desirably constructed with the "acquisition" layer made from cross-linked pulps such as are illustrated by the following European Patent applications 0 427,316 A2 and 0 427,317 A2 all by Herron et al. and U.S. Pat. No. 5,137,537 by Herron et al. assigned to Proctor & BR Gamble Co. Further, Canadian Patent application 2,035,402, by Kokko based on U.S. priority application 07/473,404 and assigned to James River Corp. likewise discloses such pulps.

Cross-linked pulps are typically prepared using formaldehyde-based compounds. More recently, polycarboxylic acids, particularly citric acid, have been shown to be effective cross-linking agents. Cross-linked fibers display excellent wet stiffness. The cross-links physically restrict the uptake of water into the fiber wall. By doing so, the fiber retains, better than conventional fiber, the characteristic stiffness of dry fibers. A web of cross-linked fibers, therefore, retains its bulk and pore volume when wet, which enhances fluid acquisition, especially with repeated wettings or insults. However, chemically cross-linked fibers are considerably more expensive than fibers which may be employed without any cross-linking. Moreover, pulps employed in prior art processes for cross-linking purposes are generally not available in sheeted form (rolls or bales of sheets).

Although pulps have been bleached under various alkaline conditions, bleaching schedules and bleaching treatment are by now those typically employed by prior art. Accordingly, a wide variety of such schedules are practiced—for the most part employing at least one or more alkaline steps at fairly high temperatures. In such sequences it has also been known to employ caustic solutions at lower temperature and then the same solution is used to bring up the temperature to or greater than a boiling point of the solution as shown in Canadian Patent 578,573 entitled "Purification of Wood Pulp" granted Jun. 30, 1959. In this patent the pulps so produced are used for dissolving pulps, i.e., making cellulose acetate and other chemical derivatives of cellulose. No description has been found concerning the improvements in absorbency, rewetting properties, stiffness of fibers, etc. as described herein for the pulps as used for the devices or products as illustrated herein. Moreover, the distinction between dissolving pulps and fluff pulp should also be noted.

BRIEF DESCRIPTION OF THE DRAWINGS

With reference to the Drawing herein.

BRIEF DESCRIPTION OF THE INVENTION

It has now been found that cold alkali extraction (CAE) of pulps such as preferably obtained from coniferous and deciduous trees results in fibers that have advantageously and unexpectedly improved absorption properties. Pulps from other source materials may also be suitable (e.g., bagasse, straw, etc.). By the term "cold" it is meant a caustic treatment not to exceed 60"C but desirably at a temperature less than 50"C but preferably at a temperature between 15"C to 40"C. By the term "caustic" it is meant sodium hydroxide solutions newly made up or as a solution by-product in a pulp or paper mill operation e.g., hemi caustic white liquor, oxidized white liquor and the like. Further, ammonium hydroxide, and potassium hydroxide and the like may be employed. However, from a cost standpoint, the preferable caustic material is sodium hydroxide.

The cold caustic extraction is typically at a caustic strength in a range from about 3% to 25%, preferably from about 6% to 18%, at a pulp consistency from about 2% to 25% but desirably from 2% to 10% but preferably from 3% to 8%. Pulps for high rate, fast absorbing applications are preferably treated with cold caustic concentrations from 13% to 18%. A wide variety of pulps are suitable such as obtained by mechanical or chemi-mechanical, sulfite, kraft, pulping reject materials, organic solvent pulps, etc. Both softwood and hardwood species are useful. Softwood pulps are preferred. Among pulps those that have not been severely bleached are useful, for example pulps with high. K Numbers (i.e., "potassium permanganate" number; a high K or Kappa Number signifies a relatively high residual lignin content for the pulp). The more heavily bleached pulp will be improved less and also requires a weaker alkali treatment. If the pulps are treated in the manner as it will be further disclosed in the specification herein, then the resulting fibers are such that these have good bulking, (i.e., "stiffness" properties) and thus have much improved absorption and rewetting properties making these pulps attractive for a number of uses. These pulps are not only characterized for their improved properties, such as by their ability to absorb and reabsorb water more quickly (than the standard untreated pulps) when subjected to multiple rewet tests, but also these pulps are useful for absorbent devices in the principal core for such device. In fact, the resulting improvements in the absorption properties are so significant that the products on an economical basis may readily compete with the more expensive prior art cross-linked products described in the above-identified patents.

Figure 3:
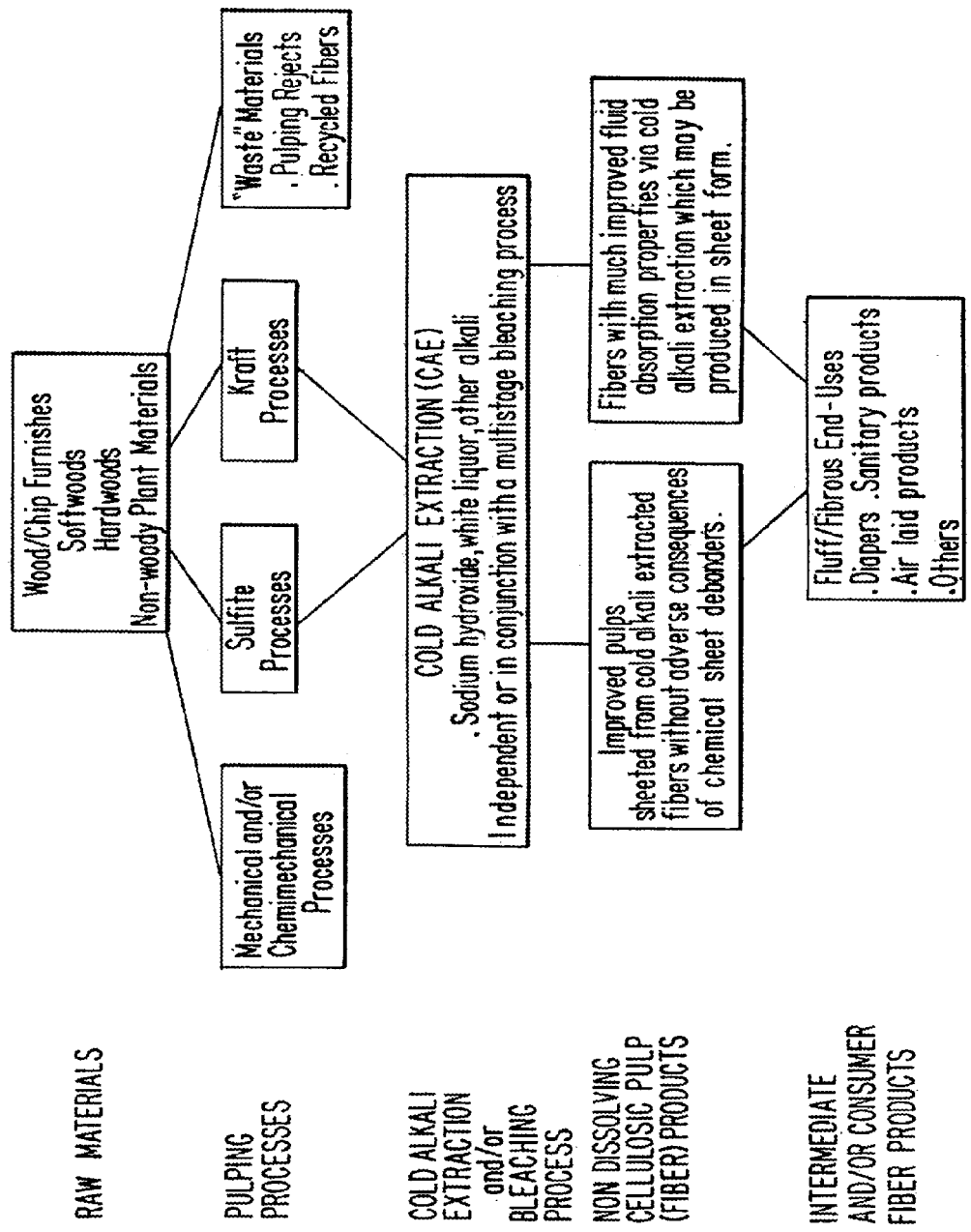
FIG. 3 is a schematic self-explanatory presentation of the overall process/product improvements.

As mentioned above, the newly discovered pulp preparation has wide applicability to all types of pulp/fiber source materials and displays improved properties for each of the pulps/fibers (FIG. 3). Upon a cold caustic treatment of the pulp/fibers, these show improved properties. For pulps prepared under different pulping conditions or processes such as sulfite, pre-hydrolyzed kraft process, conventional kraft process, organic solvent processes, or BCTMP (bleached chemi-thermal mechanical pulp), etc., the properties are invariably improved. The improved properties have been observed for all pulp and fiber types investigated. Differences, however, exist between pulps obtained from various wood species starting materials. Surprisingly, the improved properties are obtained regardless of the wood species which have been employed, for example, western hemlock, Douglas fir, Sitka spruce, Southern pine, Caribbean pine and the like. Other commercial softwood species (e.g., firs and spruces) and hardwood species (e.g., eucalyptus, poplar, beech, aspen, etc.) yield advantageous properties as well.

In an advantageous embodiment, it seems that the best characteristics for the obtained pulp have been observed for pulps that are unbleached or only slightly bleached. Nevertheless, good results have also been observed with bleached or more highly bleached pulps. As a corollary, the more highly bleached is the pulp, the lower is the caustic strength that is required to obtain the desirable effects. However, the desirable absorbency effects are somewhat less when compared on a direct basis with cold caustic extracted pulps derived from high K Number unbleached pulps (i.e. the products derived from high K Number pulps are noticeably better).

Figure 1:
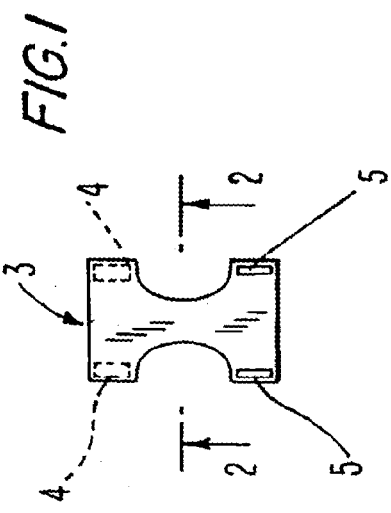
FIG. 1 is a plan view of a typical baby diaper.
Figure 2:
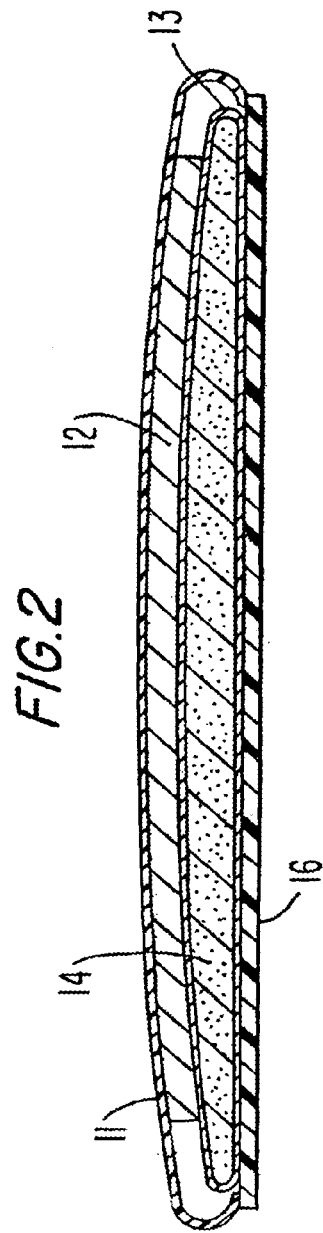
FIG. 2 is a cross-sectional view of the diaper shown in FIG. 1, along lines 2-2 thereof.

With reference to an embodiment, and the drawing herein, a typical construction of a diaper is shown in FIGS. 1 and 2 therein. In FIG. 1 the plan view of the diaper 3 in its open position shows the tabs 4 which are a part of a hook or loop component shown as 5 as its complementary element.

In FIG. 2 which shows in cross section along lines 2-2 of FIG. 1 the construction features of diaper 3 and with reference thereto from top to bottom each element in the cross section 2-2 is described as follows:

Item 11 is a thermally-bonded polypropylene coversheet. It is typically carded or spun. Item 12 is an airlaid cellulose acquisition layer. Elements 13 are tissue webs of a typical basis weight of about 16 g/m2; the absorbent core is identified as 14 and is of a fluff and SAP (super absorbent polymer and pulp mixture of a basis weight of, 500-700 g/m2). The water barrier, which is a polyethylene sheet has been shown as 16.

While the above illustration has been for a diaper, other devices have been constructed in a similar manner. Further, for similar absorbent paper products, the pulps as modified herein show substantial improvement in product performance on an economical basis. Thus, products such as catamenial and incontinence devices are improved. Other candidate applications for which the presently disclosed pulps are suitable are paper towels, sanitary tissue papers, industrial wipes, etc. For the above applications, the modified pulps may be 100% of the improved pulps as constituent pulps in the product or may be used in the product in lesser quantities, i.e., used in various admixtures with other pulp, from about 100% to about 25%.

Test Procedures

Whenever these tests have been described, the industry employed standard test procedure for the test has been used. If any changes in the procedure have been made, the changes have been described specifically.

For purposes of evaluating the pulps obtained and described by the present disclosure as well as the invention herein, several tests were used to characterize the desirable fibrous end-use performance improvements resulting from the use of cold alkali extraction and to describe some of the analytical properties of the pulp products. Also, some of the terminology used in discussing the products in the examples has been defined.

A summary of these tests and definitions follows.
Pulp Analytical Properties

The K Number or Kappa test is carried out according to TAPPI Standard Method No. T-214-SU71. This test is a measure of residual lignin content in the pulp. The test indicates the relative degree of residual lignin content in a pulp as a consequence of pulping and the extent or severity of pulping.

Pulp brightness is a measure of pulp whiteness with 100% being the maximum. Pulp brightness data here are given as ISO brightness values in %. The ISO brightness test is described in Tappi Method Number T272 (Handsheets) and T525 (Instrumentation) and uses as a measuring device a Datacolor 2000 brightness meter.
Pulp Sheet Properties Debonded pulps are fibrous end-use pulps (for example, fluff pulps) that have some chemical agent (debonder) added to inhibit interfiber bonding (addition of debonder results in a soft pulp sheet). The chemical agents, debonders, are commercial products added to fluff pulps during sheet forming which make the pulp sheet softer and easier to fluff. Debonders are closely related to fabric softeners chemically, and act in the same fashion. The force with which pulp fibers bond is measured indirectly by measuring the force (or energy) expended to debond or fluff a given pulp sheet.

The basis weight of a pulp sheet as described herein was determined on some of the products presented in the examples using a method based on TAPPI T220. A sheet of pulp, commonly 30 cm×30 cm or of another convenient dimension, was weighed and then dried to determine the solids content (%) O.D.). The area of the sheet was then determined and the ratio of O.D. (oven dried) weight to a defined area was reported as the basis weight.

The caliper and sheet density were determined on some of the products presented in the examples using a method based on TAPPI T220. Sheet calliper was determined on test specimens from the basis weight test using a motor driven micrometer that met TAPPI T41 1 conditions. Sheet density was calculated as the ratio of basis weight to caliper.

Mullen strength and burst indexes were determined on some of the products presented in the examples using a method based on TAPPI T807. A TMI Monitor Burst 1000 was used to measure the hydrostatic pressure required to rupture (bursting strength) the pulp sheet when the pressure was increased at a controlled constant rate through a rubber diaphragm to a circular area 30.5 mm diameter. Mullen strength is recorded as kPa (kilo Pascals) at rupture, while burst index is the ratio of bursting strength to basis weight.

A Kamas Lab hammermill Model H-01-C was used to defiberize some of the products presented in the examples. Strips of pulp sheets-5 cm wide were fed into the hammermill, using 900 rpm motor speed, 50% feeder speed, and an 8 mm screen. In some cases, the energy required to defiberize the pulp sheet was recorded, and reported as W hr/kg of fluff, the energy of defiberization. Fluff was collected in a collection vacuum bag for further testing.

An M/K Formation Tester was used to measure the formation of pulp sheets for some of the samples presented in the examples. The formation is an expression of sheet uniformity. The M/K Formation Tester consists of a rotating glass drum containing a traveling light source. A pulp sheet is wrapped around the outer surface of the drum. The light from inside the drum shines through the sheet and strikes a detector outside the drum. During the test, the drum rotates while the internal light source and the external detector move together down the axial length of the drum. In this way, the amount of light which passes through the sheet is measured at several different locations. The variation in the amount of light which passes through the sheet from point to point on the sheet is used as a measure of the formation (uniformity of formation) of the sheet.

Weighted average fiber length (WAFL) and fiber coarseness were also measured for some of the products presented in the examples using a Kajaani FS-200 Fiber Analyzer.

Fiber Property Performance Tests

SCAN testing of fluff pulp properties was carried out on some of the products presented in the examples. This test uses SCAN/PFI methodology (SCAN-C 33:80) and test equipment to form a uniform fluff sample, and to measure its resiliency, fluid retention and rate of absorption. The fluff samples are conditioned for at least 2 hours under standard conditions (23 t 1"C and 50%+2% relative humidity) prior to testing and are kept in the conditioning atmosphere throughout the test.

A cylindrical fluff sample (3.00 t 0.05 g and 5 cm diameter) is prepared using special equipment. The height of the cylinder under a 260 g/1.3 kPa load is measured and reported as resiliency. The sample is placed in contact with a water bath. The time required for the water to migrate vertically up the cylinder to the top is reported as absorption time. The fluid retention or absorption capacity per gram of sample is calculated by weighing the saturated fluff sample.

A fluff sample can also be subjected to simulated heat-aging artificially (105"C for two hours) and tested by this method to determine effects of aging on fluff absorbent properties.

Dry classification of fluff pulp was carried out on some of the products presented in the examples. This test is a measure of fluff quality and the defiberization process. A Johnson Manufacturing Fluff Fiberization Measuring Instrument, Model 9010, was used to separate the fluff into three fractions based on particle size. During the test, fluff is pneumatically agitated to separate the fibers from each other and from the undefibered pulpsheet. A vacuum draws the initial fines and then the long fibers through a rotating sieve screen (16 mesh, 1.18 mm opening, U.S.A. std. series). The initial fines also pass through a second screen, and accumulate in a dust bag. The long fibers (accepts) accumulate on a second screen (45 mesh, 0.36 mm opening, U.S.A. std. series).

Pad integrity testing was carried out on some of the products presented in the examples. Pad integrity is a measure of the strength of the fiber network in fluffed pulps, and indicates how well the fluff will maintain pad integrity in a dry formed absorbent product. The method is based on PFI method of 1981, "Measurement of Network. Strength in Dry, Fluffed Pulps". During the test, a cylindrical test pad of 1.0 t 0.05 gram and 50 mm diameter is prepared in a pad former. The test pad is placed in a burst chamber, which is then installed in a stress-strain apparatus. A burst-body is vertically forced through the test pad. The force required to rupture the fiber network in the test pad is reported as pad integrity.

The potential of a fibrous pulp for use as an acquisition layer can be described, among other tests, by a multiple "insult" or rewetting test. The Multiple Insult—Absorption Testing procedure was carried out as follows. Pulps for comparison purposes are fiberized, then airfiltered into pads with a basis weight of about 200 g/m2. The pads are pressed at 200 psig for a period of two minutes then trimmed about 7 cm×16 cm. The trimmed and densified pads are placed on top of a standard absorbent core, such as a disposable diaper, and covered by a single layer of conventional polypropylene coverstock. Fluid is introduced to the absorbent product through a cylinder permanently mounted to a weighted plate which applies a force of 0.1 psig to the absorbent product. A dam is used to control fluid flow to the absorbent product. A timer is started when the dam is removed and fluid begins to move into the absorbent product. The timer stops when all the fluid has been absorbed and the elapsed time recorded. Ninety seconds after the fluid is completely absorbed a stack of five pre-weighed blotter papers is placed on top and then a 1.0 psig load is applied to the absorbent product for a period of two minutes. The amount of fluid wetted back into the blotter paper is recorded. The procedure is repeated two times for a total of three wettings or 'insults'. The multiple "insult" test characterizes the readiness with which fibers absorb as well as reabsorbs a fluid.

DETAILED DESCRIPTION OF THE INVENTION AND EMBODIMENTS THEREOF

As mentioned above, it has now been found that various pulps of diverse wood species prepared by diverse pulping and bleaching processes provide improvements in these pulps by displaying improved fiber and pulp sheet properties, e.g. absorbency results such as for an acquisition layer in baby diapers, etc. upon cold alkali extraction (CAE) or cold caustic extraction (CCE) of these pulps in the proper manner in the proper sequence when preparing these pulps, i.e., when treating the pulps. Relatively high strengths of sodium hydroxide solution are used ideally, 13%-18% NaOH by weight for high absorbency, fast intensive absorbency applications and 5% to 15% for general absorbency application, preferably 6% to 10% for that purpose. By "cold caustic extraction" (CCE) is meant the treatment of pulp at a temperature less than 60° C., preferably less than about 35° C., with the above sodium hydroxide solutions. The process coextensive with the preparation of the novel pulps is being claimed as an improvement for the regime of the novel properties heretofore unrecognized in the art. The improvement thus also resides In a method for improving e.g. the absorbency of the pulp, increasing the stiffness of fibers and other properties further described herein not heretofore known or recognized.

Moreover, it has been found as an embodiment that the appropriate "acquisition layer" absorbency performance can be established after adequate bleaching of high K number unbleached pulp has been carded out to obtain aesthetically acceptable brightness values for the pulps with slightly lower cold caustic treatment (e.g. 15% NaOH versus 18% NaOH for unbleached pulps). At the lower concentration of cold caustic solution pulps are obtained which are nearly as good as pulps obtained from CCE of the high K number unbleached pulps themselves.

Accordingly, it has been found that a specific desirable pulp product regime exists, based on the process employed and the selection of various product or fiber criteria as will be further described herein. For example, the absorbency relationships make the pulps in the characterized pulp product regime especially useful because the pulps and their use can now be readily delineated from the regime of unattractive uses and pulps not possessing the attractive characteristics. Moreover, the relationships within this novel regime of other desirable properties has been established so as to delineate with great precision the claimed regime of the novel properties and the technique and process coextensive therewith.

Still further, while cold caustic treatment has been known for high quality dissolving pulps as discussed above, e.g. to make alpha cellulose and some industrial product pulps, such treatment as correlated to the fiber and pulp sheet property variables listed above is novel with respect to pulps useful such as for absorbent pulps e.g. for an acquisition layer for products inter alia diapers, incontinent and catamenial devices, etc. including absorbent core materials for these.

Added and further benefits will appear from the following examples and the illustrative embodiments. The examples are merely for the purpose of illustration and are not intended to limit the scope of the invention.

Example 1

Improved Pulp Sheet Defiberization

Debonders vs. Cold Alkali Extraction, Kraft Southern Pine Pulp

Cellulosic pulp is commonly manufactured for fluff and other fibrous end-use in dried, sheeted form. The pulp manufacturer operates the pulp machine to form the sheet from an aqueous suspension of fibers; the sheet once formed is dried to remove about 90% of the moisture. Large rolls of dried, sheeted pulp are produced off the dry end of the pulp machine. These are typically cut into smaller size rolls and/or bales of sheets for distribution to end-use customers.

It is an advantage that the dried, sheeted pulp defibers easily and uniformly without damage to the individual fibers for those pulp grades being used in various fibrous end-use applications. For example, a fluff pulp will be converted by the end-user from the dried, sheeted pulp to a pad of "fluffed" fibers by mechanical action, hereinafter sometimes referred to as "dry shredding", such as is supplied by a hammermill or other attrition mill. Chemical agents, debonders, are sometimes added to the pulp during sheet formation to inhibit interfiber bonding, which results in softer, more easily defibered sheets.

TABLE I-1

EXAMPLE 1

| SAMPLE DESCRIPTION | SAMPLE DESIGNATION | |
| --- | --- | --- |
| | A-1i | B-1i |
| Processing | Non-debonded Standard Process | Debonded Standard Process |
| Wood Species | Southern pine blend | |
| Pulping Process | Kraft | |
| Sheet Debonder Used (?) | No | Yes |
| COLD ALKALI EXTRACTION | Not Used | Not Used |
| PULP ANALYTICAL PROPERTIES | | |
| ISO Brightness, % | 88.5 | 89.4 |
| SHEET PHYSICS | | |
| Basis Wt. (g/m$^2$) | 640 | 634 |
| Caliper (mm) | 1.36 | 1.36 |
| Density (g/cm$^3$) | 0.47 | 0.47 |
| Mullen (kPa) | 1113 | 417 |
| Burst Index (kPa · m$^2$/g) | 1.74 | 0.66 |
| KAMAS FLUFF CHARACTERISTICS | | |
| Resiliency (cm) | 4.1 | 3.7 |
| Fluid Retention (g/g) | 13.4 | 11.4 |
| Absorption Time (s) | | |
| Control | 3.5 | 7.9 |
| Heat-Aged | 4.4 | 8.9 |
| Dry Classification (wt. %) | | |
| Accepts | 84.4 | 91.0 |
| Knots | 13.3 | 6.8 |
| Fines | 2.4 | 2.2 |
| Pad Integrity (N) | 7.2 | 7.0 |

TABLE II-1

EXAMPLE 1

| SAMPLE DESCRIPTION | SAMPLE DESIGNATION | |
| --- | --- | --- |
| | A-1ii | B-1ii |
| Processing | Standard Process (Non-debonded) | Cold Alkali Extraction Process |
| Wood Species | Southern pine blend | |
| Pulping Process | Kraft | |
| Sheet Debonder Used (?) | No | No |
| COLD ALKALI EXTRACTION | Not Used | Used |
| Alkali Used | | NaOH |
| Solution Strength, % | | 7.5 |
| Temperature, ° C. | | 35 |
| Time, H:M | | 10 |
| Consistency, % | | 3 |
| PULP ANALYTICAL PROPERTIES | | |
| ISO Brightness, % | 88.6 | 89.6 |

TABLE II-1-continued

EXAMPLE 1

| SAMPLE DESCRIPTION | SAMPLE DESIGNATION | |
|---|---|---|
| | A-1ii | B-1ii |
| SHEET PHYSICS | | |
| Basis Wt. (g/m$^2$) | 644 | 666 |
| Caliper (mm) | 1.12 | 1.17 |
| Density (g/cm$^3$) | 0.57 | 0.57 |
| Mullen (kPa) | 1494 | 829 |
| Burst Index (kPa·m$^2$/g) | 2.32 | 1.25 |
| KAMAS FLUFF CHARACTERISTICS | | |
| Resiliency (cm) | 4.1 | 3.6 |
| Fluid Retention (g/g) | 12.9 | 13.2 |
| Absorption Time (s) | | |
| Control | 3.3 | 2.9 |
| Heat-Aged | 4.9 | 4.6 |
| Dry Classification (wt. %) | | |
| Accepts | 81.2 | 91.4 |
| Knots | 15.9 | 6.0 |
| Fines | 2.9 | 2.7 |
| Pad Integrity (N) | 7.2 | 7.4 |

TABLE III-1

EXAMPLE 1

| SAMPLE DESCRIPTION | SAMPLE DESIGNATION | | |
|---|---|---|---|
| | A-1iii | B-1iii | C-1iii |
| Processing | Non-debonded Standard Process | Debonded Standard Process | Cold Alkali Extraction Process |
| Wood Species | Southern pine blend | | |
| Pulping Process | Kraft | | |
| Sheet Debonder Used (?) | No | Yes | No |
| COLD ALKALI EXTRACTION | Not Used | Not Used | Used |
| Alkali Used | | | NaOH |
| Solution Strength, % | | | 8.5 |
| Temperature, °C. | | | 35 |
| Time, H:M | | | 0:10 |
| Consistency, % | | | 3 |
| PULP ANALYTICAL PROPERTIES | | | |
| ISO Brightness, % | 86.6 | 88.4 | 88.9 |
| SHEET PHYSICS | | | |
| Basis Wt. (g/m$^2$) | 642 | 639 | 652 |
| Caliper (mm) | 1.36 | 1.30 | 1.33 |
| Density (g/cm$^3$) | 0.48 | 0.49 | 0.49 |
| Mullen (kPa) | 1126 | 716 | 770 |
| Burst Index (kPa·m$^2$/g) | 1.75 | 1.12 | 1.18 |
| KAMAS FLUFF CHARACTERISTICS | | | |
| Resiliency (cm) | 4.1 | 3.9 | 3.6 |
| Fluid Retention (g/g) | 13.5 | 12.4 | 12.5 |
| Absorption Time (s) | | | |
| Control | 3.3 | 7.1 | 2.5 |
| Heat-Aged | 4.3 | 7.7 | 3.0 |
| Dry Classification (wt. %) | | | |
| Accepts | 84.2 | 87.4 | 94.6 |
| Knots | 13.1 | 10.3 | 3.6 |
| Fines | 2.7 | 2.3 | 1.8 |

Table I-1 of Example 1 compares some of conventionally prepared sheet property and fluff characteristics of "non-debonded" bleached kraft Southern pine pulp (Sample A-1i) to debonded (with chemical debonder added) bleached kraft Southern pine pulp (Sample B-1i). The pulp sheet products were produced on a commercial pulp machine. The sheet properties (or sheet physics) as well as characteristics of the fluffed fiber were tested as produced by a small scale hammermill. The data given are averages of several tests on pulp from several production runs. A description of the terms and tests has been given above.

In comparison to the standard process non-debonded, sheeted pulp, the standard process debonded sheeted pulp is softer (weaker) indicated by the substantially lower pulp sheet Mullen strength as well as by the lower burst index. Note that the characteristics of the fluff from the debonded pulp are poorer as indicated by the lower resiliency, lower fluid retention, and increased (slower) absorption times compared to those of the standard pulp fluff. The dry classification data of the fluffed fibers from the debonded pulp do indicate, however, that better or more uniform defiberization was achieved (higher accepts, lower knots). The fluff pad integrity was equivalent for both types of pulp.

In Table II-1 of Example 1, pulp produced by the process of this invention, cold alkali extraction (Sample B-1ii) is compared to standard process pulp (Sample A-1ii). Both types of pulp were pulped by the kraft process from a Southern pine chip furnish and were bleached to similar brightness using standard chemicals/conditions of chlorine, chlorine dioxide, sodium hydroxide and sodium hypochlorite. The data given are mean data for several samples tested during standard production and trial production periods. The conditions used during the cold alkali extraction averaged about 7.5% NaOH solution strength, at about 35° C. for about 10 minutes at a pulp consistency of about 3%.

Note that the cold alkali extraction processed pulp sheet was softer (about 45% lower in Mullen strength and in burst index) compared to the standard process pulp sheet. Also, the dry classification data of the fluff produced upon small scale fluffing showed improvements in the greater percent accepts and in the percent lower 'knots' which indicates improved defiberability relative to the standard process pulp sheet. In these respects, the effect of the cold alkali extraction process on the pulp and fluff properties relative to the standard, non-debonded pulp were similar to the effects of the use of a chemical pulp sheet debonder relative to standard process pulp (Table I-1, Example 1) and, in fact, the novel pulps showed improved absorption properties. However, the cold alkali extraction process did not result in any negative consequences on fluff absorption times as does the use of a debonder. The fluid retention of the fluff from the cold alkali extraction processed pulp was equivalent to that of the standard pulp (Table II-1, Samples A-1ii and B-1ii).

Note that the percentage improvement was greater in the weight percent accepts (and in lower knot content) in the fluff from the cold alkali extraction process pulp compared to the fluff from standard pulp (Table II-1) than the comparable improvement associated with the use of a sheet debonder (Table I-1). The dry classification accepts were 12% greater and the knots 62% reduced for the cold alkali extraction process pulp relative to its control standard process pulp, whereas accepts for the debonded pulp were increased by only 8% with knot content reduced only 49% relative to its standard process control pulp. Also, these relative improvements were achieved by the cold alkali extraction processed pulp from a sheet that was actually somewhat harder than the debonded pulp sheet (829 Mullen strength/1.25 burst index vs. 417 Mullen strength/0.66 burst index).

The data presented in Table III-1, of Example 1 compare mill production of both debonded and non-debonded standard pulps with trial production of cold alkali extraction pulp. All pulp types (Samples A-1iii, B-1iii, and C-1iii) were produced from a Southern pine chip blend furnish by the kraft pulping process. All pulp types were bleached with chlorine dioxide, sodium hydroxide, oxygen and/or hydrogen peroxide to the brightness level indicated. The cold alkali extraction conditions achieved averaged about 8.5% NaOH solution strength, at about 35° C. for about 10 minutes applied to a pulp slurry at 3% consistency. About 0.2% $H_2O_2$ (O.D.—oven dried—pulp basis) had been added during the cold alkali extraction.

Note that the debonded pulp and the cold alkali extracted pulp sheet were produced at approximately the same Mullen strength and burst index, with both of these indicators of sheet hardness being substantially reduced for either type of treated pulp, debonded or cold alkali extracted relative to the standard process control. Again, the fluff properties for the cold alkali extracted pulp showed some similarities to the debonded standard process pulp: resiliency and fluid retention were directionally lower for both relative to the standard pulp fluff. But the absorption times for fluff from the cold alkali extracted pulp were better (faster) than for fluff from the debonded pulp or the standard process pulp. Fluff dry classification weight percentage accepts and percentage knots were better for fluff from the trial cold alkali extraction pulp.

Thus, the use of cold alkali extraction resulted in advantages not found with the standard process pulp and/or not expected from known technology of applying sheet debonders to standard process pulp as a means of "softening" the pulp sheet.

Example 2

Cold Alkali Extraction for Fiber Property Improvement, Prehydrolyzed Kraft Southern Pine Pulp The data Presented in Tables I-2 and II-2 of Example 2 illustrate the pulp sheet and fiber property improvements which occurred when cold alkali extraction was applied to pulps cooked from a Southern pine furnish by a prehydrolyzed kraft process. The prehydrolyzed kraft process is a two-stage pulping process, in which the raw material furnish is treated first under a mildly acidic condition (pH of about 3-4), followed by an alkaline stage which is basically the kraft cook illustrated in Example 1.

TABLE I-2

| EXAMPLE 2 | | |
|---|---|---|
| SAMPLE DESCRIPTION | SAMPLE DESIGNATION | |
| | A-2i | B-2i |
| Processing | Non-debonded Standard Process | Cold Alkali Extraction Process |
| Wood Species | Southern pine blend | |
| Pulping Process | Prehydrolyzed kraft | |
| Sheet Debonded Used (?) | No | No |
| COLD ALKALI EXTRACTION | Not Used | Used |
| Alkali Used | | NaOH |
| Solution Strength, % | | 15 |
| Temperature, ° C. | | 25 |
| Time, H:M | | 0:10 |
| Consistency, % | | 3 |

TABLE I-2-continued

| EXAMPLE 2 | | |
|---|---|---|
| SAMPLE DESCRIPTION | SAMPLE DESIGNATION | |
| | A-2i | B-2i |
| PULP ANALYTICAL PROPERTIES | | |
| ISO Brightness, % | 89.4 | 86.7 |
| SHEET PHYSICS | | |
| Basis Wt. (g/m$^2$) | 652 | 818 |
| Caliper (mm) | 1.32 | 1.28 |
| Density (g/cm$^3$) | 0.50 | 0.64 |
| Mullen (kPa) | 1154 | 716 |
| Burst Index (kPa · m$^2$/g) | 1.77 | 0.88 |
| KAMAS FLUFF CHARACTERISTICS | | |
| Resiliency (cm) | 3.8 | 4.0 |
| Fluid Retention (g/g) | 13.2 | 13.1 |
| Absorption Time (s) | | |
| Control | 3.4 | 3.4 |
| Heat-Aged | 4.2 | 6.1 |
| Dry Classification (wt. %) | | |
| Accepts | 95.0 | 97.3 |
| Knots | 1.8 | 0.7 |
| Fines | 3.2 | 2.0 |
| Pad Integrity (N) | 6.8 | 7.3 |
| MULTIPLE INSULT ABSORPTION TEST Absorption times, seconds | | |
| 1st Insult | 4.3 | 3.1 |
| 2nd Insult | 30.6 | 23.1 |
| 3rd Insult | 45.1 | 31.1 |

TABLE II-2

| EXAMPLE 2 | | |
|---|---|---|
| SAMPLE DESCRIPTION | SAMPLE DESIGNATION | |
| | A-2ii | B-2ii |
| Processing | Non-debonded Standard Process | Cold Alkali Extraction Process |
| Wood Species | Southern pine blend | |
| Pulping Process | Prehydrolyzed kraft | |
| Sheet Debonded Used (?) | No | No |
| COLD ALKALI EXTRACTION | Not Used | Used |
| Alkali Used | | NaOH |
| Solution Strength, % | | 10 |
| Temperature, ° C. | | 25 |
| Time, H:M | | 0:10 |
| Consistency, % | | 3 |
| PULP ANALYTICAL PROPERTIES | | |
| ISO Brightness, % | 90.5 | 87.2 |
| SHEET PHYSICS | | |
| Basis Wt. (g/m$^2$) | 847 | 897 |
| Caliper (mm) | 1.05 | 1.16 |
| Density (g/cm$^3$) | 0.81 | 0.77 |
| Mullen (kPa) | 1090 | 671 |
| Burst Index (kPa · m$^2$/g) | 1.29 | 0.75 |
| Kamas Energy (wh/kg) | 116 | 83 |
| KAMAS FLUFF CHARACTERISTICS | | |
| Resiliency (cm) | 3.8 | 3.7 |
| Fluid Retention (g/g) | 14.1 | 13.9 |

TABLE II-2-continued

EXAMPLE 2

| SAMPLE | SAMPLE DESIGNATION | |
|---|---|---|
| DESCRIPTION | A-2ii | B-2ii |
| Absorption Time (s) | | |
| Control | 4.2 | 3.8 |
| Heat-Aged | 5.6 | 5.1 |
| Dry Classification (wt. %) | | |
| Accepts | 95.3 | 95.4 |
| Knots | 1.1 | 1.4 |
| Fines | 3.6 | 3.2 |
| Pad Integrity (N) | 8.1 | 6.1 |

Sample A-2i in Table I-2 is a prehydrolyzed kraft Southern pine pulp bleached with the conventional bleaching agents of chlorine, chlorine dioxide, hypochlorite and/or hydrogen peroxide and/or oxygen and sodium hydroxide to the ISO Brightness level Indicated. Sample B-2i In Table I-2 is a similarly prehydrolyzed kraft pulp, similarly bleached to the brightness indicated prior to cold alkali extraction.

The B-2i sample's processing included the cold alkali extraction process under the conditions listed (average conditions used). Both the A-2i and B-2i samples were produced in a mill scale facility during production and trial runs, respectively.

As for the bleached Southern pine kraft pulp discussed in Example 1, the use of cold alkali extraction resulted in a softer pulp sheet (i.e., of lower Mullen strength and lower burst index). Note that the higher basis weight and density at which the B-2i sample pulp was produced should have had a negative impact on these sheet properties. In addition, the resiliency and fluid retention of the cold alkali extracted Sample B-2i were equivalent to those of Sample A-2i and the dry fluff classification results showed some improvement for Sample B-2i. Kamas fluff absorption times were similar (slightly longer for Sample B-2i upon heat-aging), but the specialized multiple insult absorption tests (described above) showed that cold alkali extraction improved the absorption properties of the resulting fiber.

The data presented in Table II-2 also compare bleached prehydrolyzed kraft Southern pine pulps (pulping conditions were more severe than those used for the samples in Table I-2 of this example).

Sample A-2ii was produced without, Sample B-2ii with cold alkali extraction. Both types were also produced In a mill-scale facility and used common bleaching techniques to reach the brightness levels indicated. The sodium hydroxide solution strength used was lower than that used for the samples described in Table I-2 of this example, 10% vs. 15%.

Comparison of sheet property data again shows the sheet softening effects resulting from the use of cold alkali extraction; lower Mullen strength, lower burst index. Also, a Kamas energy parameter (see description above) was recorded to describe the relative ease of defibering the pulp sheet during the fluffing operation in the laboratory. The cold alkali extracted pulp was fluffed more easily (with less energy input). Fluff absorptions were slightly faster for the cold caustic extracted Sample B-2ii. Dry classification of the fluffed fibers were equivalent for both samples as were resiliency and fluid retention. However, fluff pad integrity (see description above) was poorer for the cold caustic extracted Sample B (this was not the case with Sample B-2ii compared to Sample A-2i in Table I-2 of this example).

Example 3

Cold Alkali Extraction Process Variable Solution Strength

From the data given in Tables I-3 through VI-3 of this example, it is apparent that no one set of cold alkali extraction process conditions will result in exactly the same consequences on every type of pulp. Raw material/furnish used, pulping process used and the position of cold alkali extraction within a bleaching sequence have consequences on what may be the optimum conditions for each type of sample. Secondly, it appears that cold alkali extraction conditions can be selected to enhance some of the fiber properties of the resulting pulp but at the expense of others. Not all fibrous end-uses require improvements in the same properties, thus this apparent versatility of cold alkali extraction conditions might be Used to tailor pulp fibers for various fibrous end-use products and/or customers. These points will be discussed in this and subsequent examples.

TABLE I-3

EXAMPLE 3

| SAMPLE | SAMPLE DESIGNATION | | |
|---|---|---|---|
| DESCRIPTION | A-3i | B-3i | C-3i |
| Processing | Non-debonded | Cold Alkali | |
| | Standard process | Extraction Process | |
| Wood Species | Southern pine blend | | |
| Pulping Process | Kraft | | |
| K Number, mL | 18 | | |
| COLD ALKALI EXTRACTION | Not Used | Used | |
| Alkali Used | (Control) | NaOH | NaOH |
| Solution Strength, % | | 7 | 12 |
| Temperature, ° C. | | 35 | 35 |
| Time, H:M | | 0:15 | 0:15 |
| Consistency, % | | 3 | 3 |
| PULP ANALYTICAL PROPERTIES | | | |
| ISO Brightness, % | 83.3 | 92.2 | 91.4 |
| SHEET PHYSICS | | | |
| Basis Wt. (g/m$^2$) | 725 | 737 | 691 |
| Caliper (mm) | 1.75 | 2.14 | 2.41 |
| Density (g/cm$^3$) | 0.41 | 0.35 | 0.29 |
| Mullen (kPa) | 1179 | 527 | 70 |
| Burst Index (kPa · m$^2$/g) | 1.63 | 0.72 | 0.10 |
| KAMAS FLUFF CHARACTERISTICS | | | |
| Resiliency (cm) | 3.8 | 3.9 | 3.7 |
| Fluid Retention (g/g) | 13.3 | 12.2 | 14.6 |
| Absorption Time (s) | | | |
| Control | 3.7 | 2.9 | 3.9 |
| Heat-Aged | 4.3 | 3.6 | 4.1 |
| Dry Classification (wt. %) | | | |
| Accepts | 97.5 | 98.5 | 89.0 |
| Knots | 1.2 | 0.1 | 8.6 |
| Fines | 1.3 | 1.4 | 2.4 |
| Pad Integrity (N) | 6.7 | 6.4 | 5.3 |

TABLE II-3

EXAMPLE 3

| SAMPLE DESCRIPTION | SAMPLE DESIGNATION | | | |
|---|---|---|---|---|
| | A-3ii | B-3ii | C-3ii | D3ii |
| Processing | Non-debonded Standard Process | Cold Alkali Extraction Process | | |
| Wood Species | Southern pine blend | | | |
| Pulping Process | Kraft | | | |
| K Number, mL | 18 | | | |
| COLD ALKALI EXTRACTION | | | | |
| Alkali Used | None (water) | NaOH | | |
| Solution Strength, % | 0 | 3 | 7 | 14 |
| Temperature, °C. | | 35 | | |
| Time, H:M | | 0:10 | | |
| Consistency, % | | 3 | | |
| PULP ANALYTICAL PROPERTIES | | | | |
| ISO Brightness, % | 87.9 | 90.3 | 92.1 | 92.0 |
| SHEET PHYSICS | | | | |
| Basis Wt. (g/m$^2$) | 711 | 677 | 676 | 691 |
| Caliper (mm) | 1.87 | 2.03 | 2.06 | 2.79 |
| Density (g/cm$^3$) | 0.38 | 0.34 | 0.33 | 0.26 |
| Mullen (kPa) | 1189 | 1005 | 501 | 83 |
| Burst Index (kPa·m$^2$/g) | 1.67 | 1.48 | 0.75 | 0.12 |
| Kamas Energy (wh/kg) | 109.5 | 99 | 92.7 | — |
| KAMAS FLUFF CHARACTERISTICS | | | | |
| Resiliency (cm) | 3.8 | 3.5 | 3.3 | 3.3 |
| Fluid Retention (g/g) | 11.8 | 11.3 | 11.2 | 13.2 |
| Absorption Time (s) | | | | |
| Control | 4.1 | 2.8 | 2.6 | 4.0 |
| Dry Classification (wt. %) | | | | |
| Accepts | 94.6 | 94.3 | 94.0 | 75.9 |
| Knots | 2.0 | 2.7 | 3.2 | 21.1 |
| Fines | 3.4 | 3.0 | 2.8 | 3.1 |
| Pad Integrity (N) | 7.4 | 6.4 | 5.7 | 4.2 |

TABLE III-3

EXAMPLE 3

| SAMPLE DESCRIPTION | SAMPLE DESIGNATION | | | | |
|---|---|---|---|---|---|
| | A-3iii | B-3iii | C-3iii | D-3iii | E-3iii |
| Processing | Cold Alkali Extraction Process | | | | |
| Wood Species | Southern pine blend | | | | |
| Pulping Process | Prehydrolyzed kraft | | | | |
| K Number, mL | 18 | | | | |
| COLD ALKALI EXTRACTION | | | | | |
| Alkali Used | Sodium hydroxide (NaOH) | | | | |
| Solution Strength, % | 7.0 | 11.0 | 13.1 | 15.1 | 18.2 |
| Temperature, °C. | 35° C. | | | | |
| Time, H:M | 0:15 | | | | |
| Consistency, % | 3 | | | | |
| PULP ANALYTICAL PROPERTIES | | | | | |
| ISO Brightness, % | 88.0 | 88.3 | 85.3 | 85.3 | 85.7 |
| MULTIPLE INSULT ABSORPTION TESTS | | | | | |
| Absorption times, seconds | | | | | |
| 1st Insult | 7.6 | 6.6 | 6.8 | 6.2 | 6.5 |
| 2nd Insult | 37.6 | 26.2 | 25.1 | 21.8 | 22.4 |
| 3rd Insult | 56.6 | 44.9 | 36.5 | 35.0 | 33.0 |

TABLE IV-3

EXAMPLE 3

| SAMPLE | SAMPLE DESIGNATION | | | | | |
|---|---|---|---|---|---|---|
| DESCRIPTION | A-3iv | B-3iv | C-3iv | D-3iv | E-3iv | F-3iv |
| Processing | Unbleached Pulp Before Cold Alkali Extraction | Unbleached Pulp After Cold Alkali Extraction | | | | |
| Wood Species | Southern pine blend | | | | | |
| Pulping Process | Kraft | | | | | |
| K Number, mL | 8.2 | | | | | |
| COLD ALKALI EXTRACTION | Not Used | Used | | | | |
| Alkali Used | (Control) | NaOH | | | | |
| Solution Strength, % | | 6 | 9 | 12 | 15 | 18 |
| Temperature, ° C. | | 30° C. | | | | |
| Time, H:M | | 0:15 | | | | |
| Consistency, % | | 3.0 | | | | |
| MULTIPLE INSULT ABSORPTION TEST | | | | | | |
| Absorption times, seconds | | | | | | |
| 1st Insult | 8.9 | 8.2 | 6.7 | 7.5 | 7.4 | 8.3 |
| 2nd Insult | 43.8 | 43.7 | 30.7 | 32.8 | 29.6 | 31.7 |
| 3rd Insult | 64.5 | 68.5 | 51.2 | 48.3 | 50.0 | 46.3 |

TABLE V-3

EXAMPLE 3

| SAMPLE | SAMPLE DESIGNATION | |
|---|---|---|
| DESCRIPTION | A-3v | B-3v |
| Processing | Standard Process (Non-debonded) | Cold Alkali Extraction |
| Wood Species | Southern pine blend | |
| K Number, mL | 12.4 | |
| COLD ALKALI EXTRACTION | Not Used | Used |
| Alkali Used | (Control) | NaOH |
| Solution Strength | | 6 |
| Temperature, ° C. | | 28 |
| Time, H:M | | 0:15 |
| Consistency, % | | 3 |
| PULP ANALYTICAL PROPERTIES | | |
| ISO Brightness, % | 84.8 | 84.8 |
| SHEET PHYSICS | | |
| Basis Wt. (g/m$^2$) | 644 | 599 |
| Caliper (mm) | 1.33 | 1.40 |
| Density (g/cm$^3$) | 0.53 | 0.44 |
| Mullen (kPa) | 1656 | 834 |
| Burst Index (kP · m$^2$/g) | 2.63 | 1.44 |
| Kamas Energy (wh/kg) | 69.5 | 47.9 |
| KAMAS FLUFF CHARACTERISTICS | | |
| Resiliency (cm) | 4.1 | 3.7 |
| Fluid Retention (g/g) | 12.0 | 11.6 |
| Absorption Time (s) | | |
| Control | 3.2 | 2.9 |
| Heat-Aged | 4.8 | 4.5 |
| Dry Classification (wt. %) | | |
| Accepts | 86.6 | 88.7 |
| Knots | 11.8 | 9.3 |
| Fines | 1.6 | 1.9 |
| Pad Integrity (N) | 7.1 | 7.0 |

TABLE V-3-continued

EXAMPLE 3

| SAMPLE | SAMPLE DESIGNATION | | | | |
|---|---|---|---|---|---|
| DESCRIPTION | A-3vi | B-3vi | C-3vi | D-3vi | E-3vi |
| Processing | Standard Process (non-debonded) | Cold Alkali Extraction Process | | | |
| Wood Species | Southern hardwood blend | | | | |
| Pulping Process | Kraft | | | | |
| K Number, mL | 11.0 | | | | |
| COLD ALKALI EXTRACTION | | | | | |
| Alkali Used | None (control) | Sodium hydroxide | | | |
| Solution Strength, % | — | 9 | 12 | 15 | 18 |
| Temperature, ° C. | | 30° C. | | | |
| Time, H:M | | 0:15 | | | |
| Consistency, % | | 3 | | | |
| PULP ANALYTICAL PROPERTIES | | | | | |
| ISO Brightness. % | 31.5 | 43.2 | 38.6 | 37.6 | 37.8 |
| KAMAS FLUFF CHARACTERISTICS | | | | | |
| Resiliency (cm) | 3.4 | 2.9 | 2.9 | 3.0 | 2.7 |
| Fluid Retention (g/g) | 12.5 | 12.2 | 13.0 | 13.2 | 12.6 |
| Adsorption Time (s) | | | | | |
| Control | 6.2 | 4.5 | 4.0 | 4.3 | 3.8 |
| Heat-Aged | 12.9 | 8.1 | 9.3 | 7.1 | 6.5 |
| Dry Classification (wt. %) | | | | | |
| Accepts | 93.2 | 93.7 | 91.6 | 91.5 | 90.4 |
| Knots | 0.7 | 0.6 | 0.6 | 0.7 | 0.5 |
| Fines | 6.1 | 5.7 | 7.6 | 7.8 | 9.1 |
| Pad Integrity (N) | 3.6 | 4.4 | 4.1 | 4.3 | 4.1 |
| MULTIPLE INSULT ABSORPTION TEST Absorption times, seconds | | | | | |
| 1st Insult | 13.3 | 11.9 | 11.4 | 11.7 | 10.7 |
| 2nd Insult | 55.3 | 46.1 | 46.8 | 45.8 | 45.9 |
| 3rd Insult | 98.5 | 64.2 | 67.3 | 73.6 | 74.3 |

TABLE VI-3

EXAMPLE 3

| SAMPLE | SAMPLE DESIGNATION | | | | |
|---|---|---|---|---|---|
| DESCRIPTION | A-3vi | B-3vi | C-3vi | D-3vi | E-3vi |
| Processing | Standard Process (non-debonded) | Cold Alkali Extraction Process | | | |
| Wood Species | Southern hardwood blend | | | | |
| Pulping Process | Kraft | | | | |
| K Number, mL | 11.0 | | | | |
| COLD ALKALI EXTRACTION | | | | | |
| Alkali Used | None (control) | Sodium hydroxide | | | |
| Solution Strength, % | — | 9 | 12 | 15 | 18 |
| Temperature, ° C. | | 30° C. | | | |
| Time, H:M | | 0:15 | | | |
| Consistency, % | | 3 | | | |
| PULP ANALYTICAL PROPERTIES | | | | | |
| ISO Brightness, % | 31.5 | 43.2 | 38.6 | 37.6 | 37.8 |
| KAMAS FLUFF CHARACTERISTICS | | | | | |
| Resiliency (cm) | 3.4 | 2.9 | 2.9 | 3.0 | 2.7 |
| Fluid Retention (g/g) | 12.5 | 12.2 | 13.0 | 13.2 | 12.6 |
| Adsorption Time (s) | | | | | |
| Control | 6.2 | 4.5 | 4.0 | 4.3 | 3.8 |
| Heat-Aged | 12.9 | 8.1 | 9.3 | 7.1 | 6.5 |
| Dry Classification (wt. %) | | | | | |
| Accepts | 93.2 | 93.7 | 91.6 | 91.5 | 90.4 |
| Knots | 0.7 | 0.6 | 0.6 | 0.7 | 0.5 |
| Fines | 6.1 | 5.7 | 7.6 | 7.8 | 9.1 |
| Pad Integrity (N) | 3.6 | 4.4 | 4.1 | 4.3 | 4.1 |

TABLE VI-3-continued

EXAMPLE 3

| SAMPLE DESCRIPTION | SAMPLE DESIGNATION | | | | |
|---|---|---|---|---|---|
| | A-3vi | B-3vi | C-3vi | D-3vi | E-3vi |
| MULTIPLE INSULT ABSORPTION TEST Absorption times, seconds | | | | | |
| 1st Insult | 13.3 | 11.9 | 11.4 | 11.7 | 10.7 |
| 2nd Insult | 55.3 | 46.1 | 46.8 | 45.8 | 45.9 |
| 3rd Insult | 98.5 | 64.2 | 67.3 | 73.6 | 74.3 |

The data given in Table I-3 of this example cover laboratory experiments on bleached Southern pine kraft pulp. All Samples A-3i through C-3i were bleached to the brightness indicated with the common bleaching chemicals of chlorine dioxide, hydrogen peroxide and sodium hydroxide. The cold alkali extracted Sample B-3i and C-3i were additionally bleached with chlorine dioxide subsequent to cold alkali extraction (this contributed to the higher brightness levels of Samples B-3i and C-3i. The NaOH solution strength used in the cold alkali extraction of Sample B-3i was relatively low (7% compared to that used for Sample C-3i, 12%). These samples were sheeted (non-directional sheet on a laboratory sheet mold) and dried under the same standard conditions in the laboratory (but dried without restraint unlike a commercial pulp machine) so that the changes in pulp sheet and fiber/fluff properties measured reflect the cold alkali extraction process alone. Thus for Sample cold alkali extraction resulted in fibers which formed a sheet which was fluffed into fibers with the following properties relative to Sample A-3i (non-cold caustic extraction): similar basis weight, higher caliper, lower density, lower Mullen strength and lower burst index; equivalent fluff resiliency but reduced fluid retention, faster absorption times and somewhat improved dry fluff classification profiles. For Sample C-3i (cold caustic extracted at 12% NaOH solution strength) relative to Sample A-3i (non-cold caustic extracted) the comparison/contrast was as follows: slightly reduced basis weight, higher caliper, lower density, much lower Mullen strength and burst index (very weak sheet); equivalent fluff resiliency, higher fluff retention, similar Kamas fluff absorption times, and poorer dry fluid classification profile. Thus, if an end-use required a fiber of highest fluid retention, a higher caustic solution strength could be selected; to maximize accept fiber upon fluffing, a lower caustic strength would be preferable.

in Table II-3 of this Example 3, data are presented as additional data on bleached Southern pine kraft pulp, produced in the laboratory over a wider range of cold alkali extraction solution strengths. All samples A-3ii through D-3ii were bleached with the common bleaching agents of chlorine, chlorine dioxide, hydrogen peroxide and oxygen (prior to cold alkali extraction) to the ISO brightness levels indicated. Even at 3% NaOH solution strength, the pulp sheet can be somewhat softened without any large negative consequences on fluff products. However, cold caustic extraction at 14% NaOH solution strength appear to result in a pulp sheet that was fluffed with apparent negative consequences on dry classification and resiliency with no advantage in absorption time but with a slightly higher fluid retention.

Results from a similar series of bleached prehydrolyzed kraft Southern pine pulps cold caustic extracted over a range of from 7 to 18% NaOH solution strength are presented in Table III-3. All samples A-3i through E-3iii were bleached with chlorine, chlorine dioxide, sodium hypochlorite and sodium hydroxide prior to cold caustic extraction. The multiple insult absorption test results indicate that little benefit would be gained by using NaOH solution strength in the cold caustic extraction (under the temperature, time and consistency shown) greater than about 13% for this type of pulp, and that absorption times improve (decrease) progressively when using a 7% to 13% caustic solution.

Similarly, data are given in Table IV-3 of this example which illustrate a levelling off of improvement of absorption times with increasing cold alkali extraction solution strengths (6-18%). Samples B-3iv through F-3iv were all cold alkali extracted from the starting material Sample A-1v. No bleaching chemicals were used on any of the Samples A-3iv through F-3iv. Sample A-3iv was a Southern pine pulp cooked to very, very low K Number via a single stage conventional kraft cook in the laboratory. Multiple Insult absorption times of the fluff fibers were improved with the use of a 9% NaOH solution strength with no further benefit being seen above the 9% strength. Thus a similar trend toward a levelling off of absorption times with increasing solution strength seen from application of cold alkali extraction was observed for this low K Number unbleached kraft Southern pine pulp as had been observed for the bleached prehydrolyzed kraft pulp sample series given in Table III-3 of this example. But the level of the absorption times at which each type of pulp absorbed and the solution strength at which the absorption time improved occurred differently with the type of pulp extracted.

For a very low K Number bleached kraft pulp, cold alkali extraction at relatively low NaOH solution strength has many advantages other than faster absorption times. Data are given in Table V-3 of this example which compare two samples (A-3v without and B-3v with) of pulp pulped to 12.4 K Number and bleached to 84.8% ISO Brightness. The cold caustic extraction conditions used for Sample B-3v were a relatively low solution strength of 6%, at 28° C. for 15 minutes at a pulp consistency of 3%. This cold alkali extraction was used prior to bleaching to the indicated brightness. Both types of pulp samples (data averages given for A-3v and B-3v were bleached using chlorine dioxide, hydrogen peroxide and sodium hydroxide.

One of the largest drawbacks to pulping to low K Number by the kraft process is the negative consequences on fiber properties that result from the extensive pulping. Please compare the higher sheet Mullen strength and burst Index of Sample A-3v, Table V-3 to those of the samples In Tables I-3 and II-3 of this Example 3. When the processing used on the low K Number included cold alkali extraction (Sample B-3v, Table V-3), these disadvantages were overcome. In addition, the fluff characteristics of fibers from the B-3v sample low K Number pulp were equivalent to or better than the A-3v low K Number pulp sample (Table V-3, similar fluid retention, somewhat faster Kamas fluff absorption times and somewhat improved dry fluff classification profile).

In Table VI-3 of this example, data are presented for a series of unbleached kraft pulp cooked from a Southeastern United States blend of hardwoods (gums, oaks, etc.) to a low (11.0) K Number. Cold caustic NaOH solution strength was varied from 9 to 18% for Samples B-3vi through E-3vi; Sample A-3vi was the starting pulp prior, to cold alkali extraction. No bleaching chemicals were used on these samples. The 9% NaOH solution strength appears to be optimum of the conditions studied for this type of pulp in the unbleached state: Kamas fluff and multiple insult absorption times are basically constant at 9% and higher solution strengths. Dry classification profile for the fluff deteriorate at solution strengths at or above 12%. For this type of hardwood pulp, even lower NaOH strength might prove to be more desirable. Note that hardwood pulps do not match softwood pulps in these types of fibrous property performance tests. However, cold alkali extraction can be used to improve some of these fiber/fluff properties to some extent for both types of furnishes.

Example 4

Sulfite Pulps

Debonders; Cold Alkali Extraction

Debonders can be used on sulfite process pulps as well as on kraft pulps. Data are presented In Table I-4, Example 4 for commercially available sulfite pulps. The pulping process used is add sulfite (also known as acid bisulfite); both pulps are bleached to the brightness indicated by common bleaching agents such as chlorine, chlorine dioxide, hydrogen peroxide and sodium hydroxide. Data given are averaged from several tests of each type of production, non-debonded A-4i and debonded (B-4i).

TABLE I-4

EXAMPLE 4

| SAMPLE DESCRIPTION | SAMPLE DESIGNATION | |
|---|---|---|
| | A-4i | B-4i |
| Processing | Standard process non-debonded | Standard process debonded |
| Wood Species | Northwest U.S. softwood blend, predominantly Douglas fir | |
| Pulping Process | Sulfite | |
| Sheet Debonder Used (?) | No | Yes |
| COLD ALKALI EXTRACTION | Not Used | Not Used |
| PULP ANALYTICAL PROPERTIES | | |
| ISO Brightness, % | 91.8 | 91.2 |
| SHEET PHYSICS | | |
| Basis Wt. (g/m$^2$) | 698 | 684 |
| Caliper (mm) | 1.25 | 1.34 |
| Density (g/cm$^3$) | 0.56 | 0.51 |
| Mullen (kPa) | 479 | 279 |
| Burst Index (kPa · m$^2$/g) | 0.69 | 0.41 |
| Kamas Energy (wh/kg) | 41.0 | 28.7 |
| KAMAS FLUFF CHARACTERISTICS | | |
| Resiliency (cm) | 3.7 | 3.6 |
| Fluid Retention (g/g) | 13.2 | 12.1 |
| Absorption Time (e) | | |
| Control | 11.8 | 6.3 |
| Heat-Aged | 43.6 | 6.0 |
| Dry Classification (wt. %) | | |
| Accepts | 77.9 | 87.5 |
| Knots | 16.0 | 7.1 |
| Fines | 6.1 | 5.4 |
| Pad Integrity (N) | 6.3 | 6.4 |

TABLE II-4

EXAMPLE 4

| SAMPLE DESCRIPTION | SAMPLE DESIGNATION | | | |
|---|---|---|---|---|
| | A-4ii | B-4ii | C-4ii | D-4ii |
| Processing | Standard Process (non-debonded) Unbleached | Standard Process (non-debonded) Bleached | Cold Alkali Extraction Process Unbleached | Cold Alkali Extraction Process Bleached |
| Wood Species | Southern pine blend | | | |
| Pulping Process | Acid sulfite | | | |
| K Number, mL | 34 | 28 | 34 | 28 |
| COLD ALKALI EXTRACTION | Not Used | Not Used | Used | Used |
| Alkali Used | | | NaOH | NaOH |
| Solution Strength, % | | | 15 | 15 |
| Temperature, ° C. | | | 30 | 30 |
| Time, H:M | | | 0:15 | 0:15 |
| Consistency, % | | | 3 | 3 |
| PULP ANALYTICAL PROPERTIES | | | | |
| ISO Brightness, % | — | 86 | — | 86 |
| MULTIPLE INSULT ABSORPTION TEST | | | | |
| Absorption times, seconds | | | | |
| 1st Insult | 13.2 | 7.9 | 6.8 | 8.1 |
| 2nd Insult | 36.3 | 37.2 | 20.9 | 27.3 |
| 3rd Insult | 45.1 | 63.5 | 30.1 | 38.6 |

TABLE III-4

EXAMPLE 4

| SAMPLE | SAMPLE DESIGNATION | |
|---|---|---|
| DESCRIPTION | A-4iii | B-4iii |
| Processing | Standard Processing (non-debonded) | Cold Alkali Extraction Process |
| Wood Species | Caribbean Pine | |
| Pulping Process | Sulfite | |
| K Number | 24 | |
| COLD ALKALI EXTRACTION | Not Used | Used |
| Alkali Used | Not Used | NaOH |
| Solution Strength, % | | 15.4 |
| Temperature, ° C. | | 30 |
| Time, H:M | | 0:37 |
| Consistency, % | | 8 |
| PULP ANALYTICAL PROPERTIES | | |
| ISO Brightness, % | | 77.5 |
| KAMAS FLUFF CHARACTERISTICS | | |
| Resiliency (cm) | 3.4 | 2.9 |
| Fluid Retention (g/g) | 12.1 | 13.0 |
| Absorption Times (s) | | |
| Control | 2.8 | 3.5 |
| Heat-Aged | 4.4 | 4.4 |
| Dry Classification (wt. %) | | |
| Accepts | 92.4 | 80.4 |
| Knots | 1.6 | 11.3 |
| Fines | 6.0 | 8.3 |
| MULTIPLE INSULT ABSORPTION TESTS | | |
| Absorption times, seconds | | |
| 1st Insult | 38.1 | 15.9 |
| 2nd Insult | 88.2 | 45.0 |
| 3rd Insult | 135.8 | 69.6 |

TABLE IV-4

EXAMPLE 4

| SAMPLE | SAMPLE DESIGNATION | |
|---|---|---|
| DESCRIPTION | A-4iv | B-4iv |
| Processing | Standard Processing (non-debonded) | Cold Alkali Extraction Process |
| Wood Species | Douglas fir | |
| Pulping Process | Sulfite | |
| K Number, mL | 26.6 | |
| COLD ALKALI EXTRACTION | Not Used | Used |
| Alkali Used | | NaOH |
| Solution Strength, % | | 15.4 |
| Temperature, ° C. | | 30 |
| Time, H:M | | 1:00 |
| Consistency, % | | 13 |
| PULP ANALYTICAL PROPERTIES | | |
| ISO Brightness, % | — | 83.4 |
| KAMAS FLUFF CHARACTERISTICS | | |
| Resiliency (cm) | 3.5 | 2.5 |
| Fluid Retention (g/g) | 14.1 | 13.0 |
| Absorption Times (s) | | |
| Control | 4.6 | 3.8 |
| Heat-Aged | 6.2 | 4.5 |
| Dry Classification (wt %) | | |
| Accepts | 87.8 | 65.4 |
| Knots | 6.6 | 26.6 |
| Fines | 5.6 | 8.0 |
| MULTIPLE INSULT ABSORPTION TEST | | |
| Absorption times, seconds | | |
| 1st Insult | 47.2 | 28.9 |
| 2nd Insult | 103.3 | 59.9 |
| 3rd Insult | 137.9 | 77.2 |

As in the Example 1, Table I-1, which illustrated the effects of debonders on bleached kraft pulp sheet properties, debonders can act to "soften" the softwood sulfite sheet. Note the lower Mullen strength, burst Index and Kamas energy of Sample B-4i compared to Sample A-4i. There is also a similar trend toward lower fluid retention for the debonded pulp as was seen with the kraft pulp. The dry fluff classification profile is. Improved toward greater accepts, lower knots as was the case with the kraft pulp. However, sulfite pulps differ from kraft pulps in that the use of debonders improve absorption times for sulfite pulps (related to the differences in wood derived extractives in acid sulfite pulps). Note the long fluff absorption times for the non-debonded sulfite pulp.

However, for sulfite pulps the use of cold alkali extraction can have additional advantages and can improve performance in the multiple insult test. Data are given in Table II-4 of this example which compare multiple insult tests for unbleached vs. bleached sulfite Southern pine pulps, processed with and without cold alkali extraction. Samples B-4ii and D-4ii were bleached with common bleaching agents such as chlorine, chlorine dioxide, hydrogen peroxide and sodium hydroxide. Samples A-4ii and C-4ii represent two high K Number unbleached Southern pine sulfite pulps. Sample C-4ii was cold alkali extracted using the conditions indicated in Table II-4 from Sample A-4ii; Sample D-4ii was cold alkali extracted from Sample B-4ii.

These data indicate that cold alkali extraction can minimize differences in multiple insult performance of these Southern pine sulfite pulps apparent for unbleached vs. bleached pulp. Please compare the delta ($\Delta$) for first absorption times for (A-4ii to B-4ii) of 5.3 seconds, but for delta first absorption times for (D-4ii to C-4ii) of 1.3 seconds; delta for third absorption times for (B-4ii to A-4ii) of 18.4 seconds, but only a delta of 8.5 seconds for the third absorption times for (D-4ii to C-4ii). Thus cold alkali extraction reduced the magnitudes of the differences in absorption times between unbleached and bleached pulps as well as improving the actual level at which both cold caustic extracted samples C and D performed (reduced all absorption times, further discussion of these samples is given in Example 5.

Data are presented in Tables III-4 and IV-4 of Example 4 for sulfite pulps which demonstrate the effects of using relatively high sodium hydroxide solution strengths for cold alkali extraction over longer retention time and at higher consistency than were used in the previous examples and tables. All four pulp samples (A-4iii and B-4iii, Table III, A-4iv and B-4iv, Table IV) were bleached using the common pulp bleaching chemicals of chlorine dioxide, hydrogen peroxide and sodium hydroxide. Acid sulfite pulping was used to cook a Caribbean pine chip furnish to 24 K Number (Table III-4); acid sulfite pulping was used to cook Douglas fir to about 27 K Number (Table IV-4). When cold alkali extraction was used (for the B samples of both these tables, i.e., B-4iii and B-4iv), it followed an initial bleaching stage treatment of the unbleached pulp with chlorine dioxide. Bleaching was continued following the cold alkali extraction to the brightness level indicated using chlorine dioxide, hydrogen peroxide and sodium hydroxide.

For the sulfite Caribbean pine pulp, the use of cold alkali extraction at 15.4% NaOH under the conditions listed resulted in fibers showing significant improvement in the multiple insult absorption test times (all three, insult times were reduced about 50%). Kamas fluff characteristics were similar for the B-4iii sample compared to the A-4iii sample with the exception of a poorer dry classification profile for the cold caustic extracted sample B-4iii). This may be due to in optimally high NaOH solution strength for this type of pulp as was observed for some types of kraft pulps discussed under Example 4, and/or the higher consistency and/or longer time at which the relatively high concentration was used could be non-optimum.

For the sulfite Douglas fir pulp of Table IV-4, the use of cold alkali extraction also markedly improved the multiple insult absorption test times; Kamas fluff absorption times were also faster but fluff resiliency and fluid retention appeared to be more greatly affected for Caribbean pine of Table III-4. The fluff dry classification profile was also poorer with cold alkali extraction of this Douglas fir sulfite pulp. Again, as with the sulfite Caribbean pine sample and with the kraft pulp examples discussed in Example 4, these cold alkali extraction conditions may be non-optimum for fiber properties other than absorption time improvement for this type of bleached sulfite softwood fiber.

Example 5

Kraft and Sulfite Southern Pine Pulps

The following unbleached kraft pulp (Sample A-5i-Table I-5, Example 5) with a K Number of 30 was obtained from a Southern pine chip furnish. This pulp was prepared by a routine conventional kraft pulping process using methodology common to the industry. A sulfite process was used on a Southern pine chip furnish to characterize the behavior of fibers pulped from the same species via different pulping processes. This pulp was prepared by an acid bisulfite process (sulfite process) common to the industry. This pulp (Sample A-5i-Table I-5, Example 5) had a K Number of 34.

TABLE I-5

EXAMPLE 5

| SAMPLE DESCRIPTION | SAMPLE DESIGNATION | | |
|---|---|---|---|
| | A-5i | B-5i | C-5i |
| Processing | Unbleached Pulp Before Cold Alkali Extraction | Unbleached Pulp After Cold Alkali Extraction | Unbleached Pulp After Cold Alkali Extraction |
| Wood Species | Southern pine blend | | |
| Pulping Process | Kraft | | |
| K Number, mL | 30 | — | — |
| COLD ALKALI EXTRACTION | Not Used | Used | Used |
| Alkali Used | | NaOH | NaOH |
| Solution Strength, % | | 15 | 18 |
| Temperature, °C. | | 30 | 30 |
| Time, H:M | | 0:15 | 0:15 |
| Consistency, % | | 3.0 | 3.0 |
| PULP ANALYTICAL PROPERTIES | | | |
| ISO Brightness, % | — | — | — |
| MULTIPLE INSULT ABSORPTION TEST Absorption times, seconds | | | |
| 1st Insult | 9.5 | 5.6 | 5.3 |
| 2nd Insult | 36.3 | 20.2 | 18.7 |
| 3rd Insult | 56.9 | 32.4 | 26.7 |

TABLE II-5

EXAMPLE 5

| SAMPLE DESCRIPTION | SAMPLE DESIGNATION | | |
|---|---|---|---|
| | A-5ii | B-5ii | C-5ii |
| Processing | Unbleached Pulp Before Cold Alkali Extraction | Pulp After Cold Alkali Extraction | Pulp After Cold Alkali Extraction |
| Wood Species | Southern pine blend | | |
| Pulping Process | Kraft | | |
| K Number, mL | 34 | — | — |
| COLD ALKALI EXTRACTION | Not Used | Used | Used |

TABLE II-5-continued

EXAMPLE 5

| SAMPLE DESCRIPTION | SAMPLE DESIGNATION | | |
|---|---|---|---|
| | A-5ii | B-5ii | C-5ii |
| Alkali Used | | NaOH | NaOH |
| Solution Strength, % | | 15 | 18 |
| Temperature, ° C. | | 30 | 30 |
| Time, H:M | | 0:15 | 0:15 |
| Consistency, % | | 3.0 | 3.0 |
| MULTIPLE INSULT ABSORPTION TEST Absorption times, seconds | | | |
| 1st Insult | 13.2 | 6.9 | 5.1 |
| 2nd Insult | 36.3 | 24.5 | 18.6 |
| 3rd Insult | 45.1 | 32.3 | 23.2 |

TABLE III-5

EXAMPLE 5

| SAMPLE DESCRIPTION | SAMPLE DESIGNATION | | |
|---|---|---|---|
| | A-5iii | B-5iii | C-5iii |
| Processing | Bleached Pulp Before Cold Alkali Extraction | Bleached Pulp After Cold Alkali Extraction | Bleached Pulp After Cold Alkali Extraction |
| Wood Species | | Southern pine blend | |
| Pulping Process | | Kraft | |
| COLD ALKALI EXTRACTION | Not Used | Used | Used |
| Alkali Used | | NaOH | NaOH |
| Solution Strength, % | | 15 | 18 |
| Temperature, ° C. | | 30 | 30 |
| Time, H:M | | 0:15 | 0:15 |
| Consistency, % | | 3.0 | 3.0 |
| PULP ANALYTICAL PROPERTIES | | | |
| ISO Brightness, % | 92 | — | — |
| MULTIPLE INSULT ABSORPTION TEST Absorption times, seconds | | | |
| 1st Insult | 8.9 | 5.5 | 6.4 |
| 2nd Insult | 41.6 | 18.8 | 23.1 |
| 3rd Insult | 69.1 | 33.4 | 37.3 |

Despite the different pulping processes, the Southern pine chip furnish yielded fibers having excellent absorption results after cold alkali extraction (Tables I-5 and II-5 or Example 5, the alkali used being sodium hydroxide). Each of the unbleached pulps was treated with a cold caustic solution of 15% and 18% NaOH (weight %). The cold caustic extraction was carried out as follows. Pulps of 3% consistency [O.D. pulp weight/total weight (caustic solution+O.D. pulp)×100] were treated at about 30° C. for about 15 minutes by stirring the suspension. For each different caustic solution treated sample, the absorbency was determined and compared for the respective draft and sulfite pulp. It is noted that extraction with 18% NaOH gave the best test results for each of the pulp stocks.

For comparison, the unbleached kraft Southern pine pulp was bleached to an ISO brightness of 92% prior to applying the cold alkali extraction process (Sample A-5iii, Table III-5 Example 5). This pulp was the same pulp used as the starting material for bleaching in Example 5 (Sample A-5i, Table I-5). However, prior to cold caustic extraction it was bleached with the chemicals of chlorine, chlorine dioxide, hydrogen peroxide, oxygen and sodium hydroxide. The results obtained are shown In Table III-5 when following the same cold caustic extraction procedure as outlined above.

From the comparison of the data in Tables I-5 and II-5 of this example, it is evident that for the unbleached pulp an increase in concentration of the cold caustic solution to 18% NaOH improved the absorption properties; for bleached pulp (Sample A-5iii, Table III-5) the higher concentration (i.e., 18% NaOH reduced the absorbency properties compared to extraction with 15% NaOH. However, note that the absorbency properties of the bleached pulp cold caustic extracted with 15% NaOH were distinctly better than those of the bleached pulp processed without any cold alkali extraction.

Example 6

Prehydrolyzed Kraft Bleached Southern Pine Pulp

In a manner similar to that used for Example 5, the absorption properties were determined for a bleached, prehydrolyzed kraft pulp from Southern pine wood. This pulp was prepared by a routine prehydrolyzed kraft pulping process using methodology common to the industry and was bleached using the chemicals of chlorine, chlorine dioxide, sodium hydroxide, and sodium hypochlorite to an ISO Brightness of 86%. The K Number of the unbleached pulp was about 18 mL.

TABLE I-6

EXAMPLE 6

| SAMPLE DESCRIPTION | SAMPLE DESIGNATION | | |
|---|---|---|---|
| | A-6i | B-6i | C-6i |
| Processing | Bleached Pulp Before Cold Alkali Extraction | Bleached Pulp After Cold Alkali Extraction | Bleached Pulp After Cold Alkali Extraction |
| Wood Species | Southern pine | | |
| Pulping Process | Steam prehydrolyzed Kraft | | |
| COLD ALKALI EXTRACTION | Not Used | Used | Used |
| Alkali Used | | NaOH | NaOH |
| Solution Strength, % | | 15 | 18 |
| Temperature, ° C. | | 30 | 30 |
| Time, H:M | | 0:15 | 0:15 |
| Consistency, % | | 3.0 | 3.0 |
| PULP ANALYTICAL PROPERTIES | | | |
| ISO Brightness, % | 86 | — | — |
| MULTIPLE INSULT ABSORPTION TEST Absorption times, seconds | | | |
| 1st Insult | 6.7 | 4.9 | 6.2 |
| 2nd Insult | 46.6 | 19.6 | 25.5 |
| 3rd Insult | 77.2 | 32.3 | 41.9 |

The absorption results after cold alkali extracting this pulp with 15% and 18% NaOH are shown in Table I-6, and confirm the effect caused by CCE treatment on the absorbency of the pulp. Again, this pine pulp subjected to extraction after bleaching with 15% NaOH (Sample A-6i, Table I-6, Example 6) gave better results than that extracted with 18% NaOH.

In comparison to the absorption property data given in Example 5, Tables I-5 to III-5, the absorption test results for the prehydrolyzed kraft Southern pine fiber show that these are within a good range of absorbency despite having been bleached to this relatively high brightness prior to cold alkali extraction.

Example 7

Kraft Southern Pine Pulp

Unbleached K Number Interaction

The accompanying Table I-7, Example 7, Illustrates a comparative series of kraft Southern pine pulps where unbleached pulp K Number was varied (relative severity of pulping—low numbers indicate a more drastic pulping schedule with less lignin remaining in the pulp after pulping). In order to establish the desired pulp property regime and pulping procedures, the bleaching of all three unbleached stocks was carried out to equivalent brightness (92% ISO). The bleaching chemicals of chlorine, chlorine dioxide, hydrogen peroxide, oxygen and sodium hydroxide were used. It is noted that as unbleached K Number increased, resulting absorption properties after cold caustic extraction improved (lower absorption times are better).

TABLE I-7

EXAMPLE 7

| SAMPLE DESCRIPTION | SAMPLE DESIGNATION | | | | | |
|---|---|---|---|---|---|---|
| | A-7i | B-7i | C-7i | D-7i | E-7i | F-7i |
| Processing | Bleached Pulp Before Cold Alkali Extraction | Bleached Pulp After Cold Alkali Extraction | Bleached Pulp Before Cold Alkali Extraction | Bleached Pulp After Cold Alkali Extraction | Bleached Pulp Before Cold Alkali Extraction | Bleached Pulp After Cold Alkali Extraction |
| Wood Species | Southern pine | | | | | |
| Pulping Process | Kraft | | | | | |
| K Number, mL | 19 | — | 22 | — | 30 | — |
| COLD ALKALI EXTRACTION | Not Used | Used | Not Used | Used | Not Used | Used |
| Alkali Used | | NaOH | | NaOH | | NaOH |
| Solution Strength, % | | 15 | | 15 | | 15 |
| Temperature, ° C. | | 30 | | 30 | | 30 |
| Time, H:M | | 0:15 | | 0:15 | | 0:15 |
| Consistency, % | | 3.0 | | 3.0 | | 3.0 |
| PULP ANALYTICAL PROPERTIES | | | | | | |
| ISO Brightness, % | 92 | — | 92 | — | 92 | — |
| MULTIPLE INSULT ABSORPTION TEST | | | | | | |
| Absorption times, seconds | | | | | | |
| 1st Insult | 8.6 | 6.7 | — | 5.9 | 8.9 | 5.5 |
| 2nd Insult | 46.3 | 29.6 | — | 26.9 | 41.6 | 18.8 |
| 3rd Insult | 75.0 | 45.5 | — | 39.8 | 69.1 | 33.4 |

Example 8

Sitka Spruce Sulfite Pulp

In a manner similar to that used for the Southern pine chip furnish, spruce starting material was sulfite pulped. The sulfite process used was acid sulfite (also known as acid bisulfite) as in Example 5. The unbleached pulp was subjected to cold caustic extraction. Data for the cold caustic extracted pulps treated with 15% and 18% NaOH are shown in Table I-8, Example 8. It is noted that while not all starting pulps perform at the same level, nevertheless there was a significant improvement in absorbency after cold caustic solution treatment for each of the pulps obtained from this species. Both spruce pulp Samples B-8i and C-8i performed similarly (no significant difference between 15% NaOH and 18% NaOH extractions).

TABLE I-8

EXAMPLE 8

| SAMPLE DESCRIPTION | SAMPLE DESIGNATION | | |
|---|---|---|---|
| | A-8i | B-8i | C-8i |
| Processing | Unbleached Pulp Before Cold Alkali Extraction | Unbleached Pulp After Cold Alkali Extraction | Unbleached Pulp After Cold Alkali Extraction |
| Wood Species | Sitca Spruce | | |
| Pulping Process | Sulfite | | |
| K Number, mL | 31 | — | — |
| COLD ALKALI EXTRACTION | Not Used | Used | Used |
| Alkali Used | | NaOH | NaOH |
| Solution Strength, % | | 15 | 18 |
| Temperature, ° C. | | 30 | 30 |
| Time, H:M | | 0:15 | 0:15 |
| Consistency, % | | 3.0 | 3.0 |
| PULP ANALYTICAL PROPERTIES | | | |
| ISO Brightness, % | — | — | — |
| MULTIPLE INSULT ABSORPTION TEST | | | |
| Absorption times, seconds | | | |
| 1st Insult | 70.0 | 12.2 | 10.0 |
| 2nd Insult | 43.7 | 22.3 | 24.1 |
| 3rd Insult | 64.8 | 33.6 | 33.2 |

Example 9

Western Hemlock Sulfite Pulp

This example illustrates the absorption properties obtained for a pulp made from a western hemlock chip furnish by a sulfite pulping process (acid sulfite). Cold caustic extraction of the bleached hemlock pulp (ISO Brightness=88%) again illustrates the improvement that results on cold alkali treatment: greater speed of absorbency of fibers produced by cold caustic solution extraction. The data are given in Table I-9, Example 9.

TABLE I-9

| SAMPLE | EXAMPLE 9 | | |
|---|---|---|---|
| | SAMPLE DESIGNATION | | |
| DESCRIPTION | A-9i | B-9i | C-9i |
| Processing | Bleached Pulp Before Cold Alkali Extraction | Bleached Pulp After Cold Alkali Extraction | Bleached Pulp After Cold Alkali Extraction |
| Wood Species | Western Hemlock | | |
| Pulping Process | Sulfite | | |
| K Number, mL | — | — | — |
| COLD ALKALI EXTRACTION | Not Used | Used | Used |
| Alkali Used | | NaOH | NaOH |
| Solution Strength, % | | 15 | 18 |
| Temperature, ° C. | | 30 | 30 |
| Time, H:M | | 0:15 | 0:15 |
| Consistency, % | | 3.0 | 3.0 |
| PULP ANALYTICAL PROPERTIES | | | |
| ISO Brightness, % | 88 | — | — |
| MULTIPLE INSULT ABSORPTION TEST | | | |
| Absorption times, seconds | | | |
| 1st Insult | 12.3 | 7.7 | 9.4 |
| 2nd Insult | 47.2 | 31.9 | 39.9 |
| 3rd Insult | 75.1 | 44.7 | 62.0 |

Example 10

BCTMP (Bleached Chemi-Thermal Mechanical Pulp) and Cold Alkali Extraction

In this example, BCTMP (a bleached chemi-thermal mechanical pulp) commercially available from Tembec Co. was also extracted with 15% and 18% NaOH. The absorption test data (Table I-10, Example 10) show substantial improvement at the higher cold caustic solution strength. The K Number of this BCTMP pulp was 36 mL. Even higher caustic solution strengths (e.g., about 20%) may prove to be beneficial to absorbent property performance for fibers produced from this type of furnish via this pulping process. The wood furnish is a North American, eastern Canadian softwood. Description of chemi-thermal mechanical pulping and bleaching processes can be found in texts on, pulping and bleaching.

TABLE I-10

| SAMPLE | EXAMPLE 10 | | |
|---|---|---|---|
| | SAMPLE DESIGNATION | | |
| DESCRIPTION | A-10i | B-10i | C-10i |
| Processing | Bleached Pulp Before Cold Alkali Extraction | Unbleached Pulp After Cold Alkali Extraction | Unbleached Pulp After Cold Alkali Extraction |
| Wood Species | Northern Softwood | | |
| Pulping Process | Bleached Chemi-thermal mechanical | | |
| K Number, mL | 36 | — | — |
| COLD ALKALI EXTRACTION | Not Used | Used | Used |

TABLE I-10-continued

EXAMPLE 10

| SAMPLE DESCRIPTION | SAMPLE DESIGNATION | | |
|---|---|---|---|
| | A-10i | B-10i | C-10i |
| Alkali Used | | NaOH | NaOH |
| Solution Strength, % | | 15 | 18 |
| Temperature, ° C. | | 30 | 30 |
| Time, H:M | | 0:15 | 0:15 |
| Consistency, % | | 3.0 | 3.0 |
| PULP ANALYTICAL PROPERTIES | | | |
| ISO Brightness, % | — | — | — |
| MULTIPLE INSULT ABSORPTION TEST | | | |
| Absorption times, seconds | | | |
| 1st Insult | 9.7 | 8.8 | 4.0 |
| 2nd Insult | 39.8 | 37.8 | 25.1 |
| 3rd Insult | 61.2 | 59.8 | 35.4 |

Example 11

Use of Cold. Alkali Extraction on Semi-Bleached, Lower Brightness Pulp

The strength of caustic solution required to achieve optimum absorption properties is related to the type of raw material and to pulping and bleaching steps used. In general, however, the less bleached (lower brightness) the pulp, the higher the concentration of NaOH solution required to achieve optimum properties. Also, the absorption properties attained are better when the pulp is less bleached prior to application of a cold caustic treatment. This is illustrated below in Table I-11, Example 11, where two Southern pine kraft pulps bleached to different brightness levels (ISO Brightness of 51 and 88, respectively) underwent cold alkali extraction with 15 and 18% NaOH solutions. The results for both of these pulps show that 15% NaOH gave the best overall absorption time results (third insult time is the most significant one) with the pulp of lower brightness (semi-bleached pulp) yielding superior properties.

TABLE I-11

EXAMPLE 11

| SAMPLE DESCRIPTION | SAMPLE DESIGNATION | | | |
|---|---|---|---|---|
| | A-11i | B-11i | C-11i | D-11i |
| Processing | Semi-Bleached Pulp (ISO Brightness = 51%)[a] After Cold Alkali Extraction | | Bleached Pulp (ISO Brightness = 51%)[b] After Cold Alkali Extraction | |
| Wood Species | Southern pine blend | | | |
| Pulping Process | Kraft | | | |
| COLD ALKALI EXTRACTION | Used | Used | Used | Used |
| Alkali Used | | NaOH | | |
| Solution Strength, % | 15 | 18 | 15 | 18 |
| Temperature, ° C. | 30 | 30 | 30 | 30 |
| Time, H:M | 0:15 | 0:15 | 0:15 | 0:15 |
| Consistency, % | 3.0 | 3.0 | 3.0 | 3.0 |
| MULTIPLE INSULT ABSORPTION TEST | | | | |
| Absorption times, seconds | | | | |
| 1st Insult | 5.0 | 3.8 | 6.2 | 4.9 |
| 2nd Insult | 22.1 | 21.2 | 22.2 | 24.8 |
| 3rd Insult | 25.1 | 36.7 | 33.9 | 38.6 |

[a]Prepared by bleaching Sample A-11i of Example 11 (Table 11) with chlorine, chlorine dioxide, hydrogen peroxide, oxygen and sodium hydroxide to an ISO Brightness of 51.

[b]Prepared by bleaching Sample A-11i of Example 11 (Table 11) with chlorine, chlorine dioxide, hydrogen peroxide, oxygen and sodium hydroxide to an ISO Brightness of 88.

TABLE II-1

EXAMPLE 11

| SAMPLE DESCRIPTION | SAMPLE DESIGNATION | | | |
|---|---|---|---|---|
| | A-11ii | B-11ii | C-11ii | D-11ii |
| Processing | Semi-Bleached Pulp (ISO Brightness = 38%)[a] After Cold Alkali Extraction | | Semi-Bleached Pulp (ISO Brightness = 44%)[a] After Cold Alkali Extraction | |
| Wood Species | Southern pine blend | | | |
| Pulping Process | Sulfite | | | |
| K Number, mL | — | — | — | — |
| COLD ALKALI EXTRACTION | Used | Used | Used | Used |
| Alkali Used | NaOH | | | |
| Solution Strength, % | 15 | 18 | 15 | 18 |
| Temperature, ° C. | 30 | | | |
| Time, H:M | 0:15 | | | |
| Consistency, % | 3.0 | | | |
| MULTIPLE INSULT ABSORPTION TEST Absorption times, seconds | | | | |
| 1st Insult | 4.5 | 4.5 | 5.8 | 4.7 |
| 2nd Insult | 24.5 | 18.8 | 24.1 | 20.2 |
| 3rd Insult | 36.4 | 30.2 | 41.1 | 31.2 |

[a]Prepared by bleaching Sample A-5ii of Example 5 (Table II-5) with chlorine dioxide, hydrogen peroxide and sodium hydroxide.

All of the Samples A-11i through D-11i (Table I-11, Example 11) were prepared by bleaching the 30K Number Southern pine kraft pulp discussed in Example 5 (Sample A-5i, Table I-5) to the brightness level indicated, and then cold caustic extracted under the conditions indicated. Note that in the unbleached state, 18% NaOH resulted in better absorption properties and that these absorption times were better than those associated with semi-bleached pulps described in Table I-11, Example 11.

When the 34 K Number unbleached Southern pine sulfite pulp of Example 5, Table II-5 (Sample A-5ii) was semi-bleached to ISO Brightness levels of 38 and 44, respectively, prior to cold caustic extraction with 15 and 18% NaOH, 18% NaOH was still required to give optimum absorption properties. The results of this work are seen in Table II-11, Example 11. Note that less bleached pulp (ISO Brightness=38%) still gives the best results when extracted with 18% NaOH (Sample B-11ii versus Sample D-11ii); the results, however, are not as good as those observed by 18% NaOH extraction of the unbleached pulp itself with 18% NaOH (see results for Sample C-5ii, Table II-5, Example 5).

Example 12

Position of Cold Alkali Extraction in a Multistage Bleach Sequence

The benefits of cold caustic extraction in improving absorbency occurs regardless of where it is applied in the bleaching sequence (e.g., at the beginning, the middle, or at the very end). In the same multi-stage bleaching sequence to prepare high brightness pulps there is even some indication that when the same quantity of chemicals are used, there may be improved absorption properties by applying the stage in the middle of the sequence. Such an example is now presented in which the only bleaching variable, in a 5-stage sequence to prepare a fully bleached pulp from the same unbleached stock, was the position of the CCE stage in the sequence; 15% NaOH solution strength was used.

TABLE I-12

EXAMPLE 12

| SAMPLE DESCRIPTION | SAMPLE DESIGNATION | | |
|---|---|---|---|
| | A-12i | B-12i | C-12i |
| Processing | Fully Bleached Pulp (5 Bleach Stages) with Cold Alkali Extraction In Stage 1 | Fully Bleached Pulp (5 Bleach Stages) with Cold Alkali Extraction In Stage 3 | Fully Bleached Pulp (5 Bleach Stages) with Cold Alkali Extraction In Stage 5 |
| Wood Species | Southern pine | | |
| Pulping Process | Prehyrdolyzed kraft | | |
| COLD ALKALI EXTRACTION | Used | | |
| Alkali Used | NaOH | | |
| Solution Strength, % | 15 | | |
| Temperature, ° C. | 30 | | |
| Time, H:M | 0:15 | | |
| Consistency, % | 3.0 | | |

TABLE I-12-continued

EXAMPLE 12

| SAMPLE | SAMPLE DESIGNATION | | |
|---|---|---|---|
| DESCRIPTION | A-12i | B-12i | C-12i |
| PULP ANALYTICAL PROPERTIES | | | |
| ISO Brightness, % | 84 | 87 | 84 |
| MULTIPLE INSULT ABSORPTION TEST Absorption times, seconds | | | |
| 1st Insult | 17.7 | 14.4 | 19.2 |
| 2nd Insult | 44.5 | 31.2 | 43.4 |
| 3rd Insult | 67.7 | 57.2 | 70.4 |

The results shown above (Table II-12) Indicate that when CCE was used in the middle of the sequence (stage 3), the absorption time results were clearly better (Sample B-12i) than when CCE was used in the 1st or 5th stages. It was interesting to note that ISO Brightness of the fully bleached pulp (Sample B-12i) was also improved relative to the other two (i.e., 87 versus 84%).

Example 13

Kraft Pulping Reject Material

In an effort to look at pulp that is even "rawer" or less pulped than what normally occurs in conventional full chemical pulping processes, some "knots" resulting from a conventional kraft cook of Southern pine chip furnish were cold caustic extracted with 18% NaOH. "Knots" essentially represent pulping reject materials that are poorly cooked (relatively large in size unlike shives and separable from the resulting pulped fibers via equipment loosely termed "knotters"). It was necessary to first defiber these knots in a Waring blender and to flat screen this defibered material to remove reject material still remaining non-defibered prior to cold alkali extraction with 18% NaOH. The fibers had a very high K Number (>50).

TABLE I-13

EXAMPLE 13

| SAMPLE DESCRIPTION | SAMPLE DESIGNATION A-13i |
|---|---|
| Processing | Defiberized Knots (Rejects) After Cold Alkali Extraction |
| Wood Species | Southern pine blend |
| Pulping Process | Kraft |
| K Number, mL (80 mL test) | >50 |
| COLD ALKALI EXTRACTION | Used |
| Alkali Used | NaOH |
| Solution Strength, % | 18 |
| Temperature, ° C. | 30 |
| Time, H:M | 0:15 |
| Consistency, % | 3.0 |
| PULP ANALYTICAL PROPERTIES | |
| ISO Brightness, % | — |

TABLE I-13-continued

EXAMPLE 13

| SAMPLE DESCRIPTION | SAMPLE DESIGNATION A-13i |
|---|---|
| MULTIPLE INSULT ABSORPTION TEST Absorption times, seconds | |
| 1st Insult | 5.4 |
| 2nd Insult | 13.9 |
| 3rd Insult | 25.9 |

The multiple insult absorption test results shown in Table I-13, Example 13 indicate that these type of fibers after cold alkali extraction exhibit good absorption times. The absorption times are equivalent to those of the cold alkali extraction 30 K Number unbleached kraft Southern pine pulp (Sample C-5i, Table I-5, Example 5) and to those of the cold alkali extracted 34 K Number unbleached Southern pine sulfite pulp (Sample C-5i, Table II-5, Example 5), despite the raw material being essentially a waste material A cold caustic extraction would add significant value in turning this waste fiber into a viable absorbent product.

It is believed that similar results would be obtained by stopping the initial kraft pulping process at a point(s) corresponding to less delignification overall and combining mechanical defiberization and screening steps prior to cold alkali extraction and/or any bleaching desired to increase brightness (i.e., semi-chemical rather than full chemical pulping).

Example 14

Alkali Source Other Than Sodium Hydroxide Kraft White Liquor

A potential source of sodium hydroxide within a kraft pulp mill is white liquor used in the kraft pulping process. White liquor is a mixture of sodium hydroxide and sodium sulfide. A suggestion is to carry out cold alkali extraction using the alkali present in white liquor (WL) as the source of NaOH; it is also possible that the sodium sulfide present in the white liquor will have some positive benefits. In Table I-14, Example 14, are presented results of extraction of an unbleached Southern pine kraft pulp with 9-18% NaOH In which some or almost all of the NaOH requirements in the cold caustic extraction came from the white liquor itself (the contribution of sodium sulfide to alkalinity was ignored). For comparative purposes, cold caustic extractions with 9, 15 and 18% NaOH solutions were also carried out as controls (Samples F-14i, G-14i, and H-14i, Table I-14).

TABLE I-14

EXAMPLE 14

| SAMPLE DESCRIPTION | SAMPLE DESIGNATION | | | | | | | |
|---|---|---|---|---|---|---|---|---|
| | A-14i | B-14i | C-14i | D-14i | E-14i | F-14i | G-14i | H-14i |
| Processing | Unbleached Pulp Before Cold Alkali Extraction | Unbleached Pulp After Cold Alkali Extraction with White Liquor (WL)[a] | | | | Unbleached Pulp After Cold Alkali Extraction (Control) | | |
| Wood Species | | | | Southern pine | | | | |
| Pulping Process | | | | Kraft | | | | |
| K Number, mL | | | | 18.7 | | | | |
| COLD ALKALI EXTRACTION | Not Used | | | | Used | | | |
| Alkali Used | (Control) | NaOH (96% from WL) | NaOH (67% from WL) | NaOH (48% from WL) | NaOH (37% from WL) | NaOH | NaOH | NaOH |
| Solution Strength, % | | 9 | 12 | 15 | 18 | 9 | 15 | 18 |
| Temperature, °C. | | | | | 30 | | | |
| Time, H:M | | | | | 0:15 | | | |
| Consistency, % | | | | | 3.0 | | | |
| MULTIPLE INSULT ABSORPTION TEST Absorption times, seconds | | | | | | | | |
| 1st Insult | 7.0 | 8.7 | 6.5 | 6.5 | 6.7 | 8.0 | 7.0 | 5.9 |
| 2nd Insult | 37.2 | 25.3 | 23.7 | 25.0 | 24.3 | 30.4 | 26.1 | 26.8 |
| 3rd Insult | 60.7 | 42.2 | 37.3 | 38.9 | 37.6 | 50.5 | 35.9 | 37.0 |

[a]Effective alkali (NaOH wt. %) = 9.29.

The use of white liquor to supply alkali was equivalent to the use of sodium hydroxide at 15 and 18% NaOH solution strength (compare Samples C-14i and G-14i, D-14i and H-14i, Table I-14, Example 14) in achieving improved absorption properties relative to those of the non-cold alkali extracted unbleached Southern pine kraft pulp. At 9% solution strength, the use of white liquor appeared to result in some improvement over the use of NaOH alone (compare Sample B-14i to F-14i, Table I-14i, Example 14). It is believed that at even lower alkali solution strengths white liquor may also result in advantages over the use of sodium hydroxide alone.

Example 15

Use of Hemi Caustic for Cold Alkali Extraction

In using sodium hydroxide for cold alkali extraction, a caustic solution is obtained which contains some organic material removed or "extracted" from the pulp. This type of caustic solution is termed "hemi caustic". The organic materials solubilized during the cold alkali reaction with the pulp are considered to be predominantly hemicellulosic materials (hemicelluloses are non-cellulosic carbohydrate materials composed of xylan, mannan, araban, etc. monomers rather than the glucose monomer of cellulose). For a fibrous end-use pulp, cold alkali extraction may also remove some of these hemicelluloses or other organics. However, the desired end-result is not chemically purer pulp fibers. Purity is required in dissolving pulps because these pulps must function as chemical feedstocks in chemical end-use processes (esters such as acetates, butyrates and nitrates, ethers, regenerated cellulose, etc). For a fibrous end-use application, the end result desired from the use of cold alkali extraction is that the fibers produced exhibit improved performance as fibers—as fluffed fibers in absorbent products, etc. such appreciation of the desired end result heretofore has not been recognized or known.

TABLE I-15

EXAMPLE 15

| SAMPLE DESCRIPTION | SAMPLE DESIGNATION | | |
|---|---|---|---|
| | A-15i | B-15i | C-15i |
| Processing | Standard Process (Bleached Pulp prior to Cold Alkali Extraction) | Cold Alkali Extraction (Bleached Pulp subsequent to Cold Alkali Extraction) | |
| Wood Species | | Southern pine blend | |
| Pulping Process | | Kraft | |
| K Number, mL | | 17.4 | |
| COLD ALKALI EXTRACTION | Not Used | | Used |
| Alkali Used | (Control) | 100% NaOH | 100% hemicaustic |
| Solution Strength, % | | | 15 |
| Temperature, °C. | | | 30 |

TABLE I-15-continued

EXAMPLE 15

| SAMPLE DESCRIPTION | SAMPLE DESIGNATION | | |
|---|---|---|---|
| | A-15i | B-15i | C-15i |
| Time, H:M | | | 0:15 |
| Consistency, % | | | 3.0 |
| PULP ANALYTICAL PROPERTIES | | | |
| ISO Brightness, % | 84.5 | 85.5 | 84.4 |
| MULTIPLE INSULT ABSORPTION TEST Absorption times, seconds | | | |
| 1st Insult | 4.7 | 4.9 | 4.9 |
| 2nd Insult | 25.6 | 18.8 | 20.4 |
| 3rd Insult | 44.8 | 29.9 | 36.6 |

The data presented in Example 15, Table I-15 show that hemi caustic (i.e., caustic separated from the pulp after reaction under an initial pure sodium hydroxide cold caustic extraction) can be reused to supply the alkali source for subsequent cold caustic extractions for pulps with improvements in absorbency properties. Absorption times are improved relative to the non-cold caustic extracted bleached Southern pine kraft pulp when the alkali source used was either sodium hydroxide or hemi caustic. The hemi caustic solution used was at 24.5% sodium hydroxide by weight and contained 2.9% "hemicellulose" material. The improvements when the hemi caustic was used were not as great as those when pure sodium hydroxide was used. However, it is expected that some modification of the cold caustic extraction conditions (for example, increasing the solution strength when hemi caustic is used) would make the effects of both types of caustic equivalent.

It would also follow that other alkali sources when used in initially contacting the pulp in a cold alkali extraction could be reused in subsequent extraction for these types of fibrous end-use non-dissolving pulps.

In the above Examples the cold caustic solution treatment or cold caustic extraction of the pulp was typically at the indicated solution strength, at 3.0% consistency, for 15 minutes at 30° C., followed by a fresh water rinse (30° C.), an acid wash (typically a sulfuric acid solution at pH of about 3) and a final fresh water rinse.

Other test data that were obtained also indicate that for the entire range of concentration of the cold caustic solution, the concentration may range between about 5% to 25% and higher but 13% to 18% gave the best results for the various pulp starting materials utilized for acquisition layers, i.e. intensive, fast absorption uses. A suitable concentration is dependent on the relative severity of bleaching with, the more severely bleached pulps requiring a milder treatment. For absorbency improvements in general and also for improving yields and other fluff pulp properties lower concentrations of caustic may be used i.e. to about 5%. The versatility of the process has also been demonstrated for a variety of pulp source materials.

As illustrated above and while in the examples the cold caustic solution has been a sodium hydroxide solution, other alkali materials may be used. Other alkali materials such as potassium hydroxide etc. may be used but at a severe economic penalty such that their use is prohibitive.

Likewise, a combination of sodium hydroxide solution and a water soluble, non-toxic glycol, (e.g., propylene glycol solution) might also be used, but the added cost is less justified for this large volume bulk product.

In describing the regime for the acceptable starting pulps and process conditions for CCE treatment, this regime may be characterized as follows: for fast absorbency improvements such as measured by the insult tests, especially the third insult, the K Number related to absorbency and severity of pulping, the severity of pulping which may be avoided when practicing the present utilization of various pulps in bleached and unbleached conditions, enhanced yields and advantageous use of reject materials, use of mill by-products, swing capability to insert in the bleaching treatment steps the CCE step in any bleaching sequence, fluff pulp properties not requiring debonders, i.e. without additives, etc. etc. Such improvements especially in combination with each other have heretofore not been recognized, known or practiced for fluff pulps and thus have not shown the way to the unique combination(s) of properties described above.

The basis weight of acquisition layers in current products ranges from 75 to 200 $g/m^2$. As an example, the acquisition layer 12 shown In FIG. 2 is an air laid fluff web of 200 $g/m^2$. This web is separated from the absorbent core 13 by a layer of conventionally wet-laid tissue paper 13. The core may be wrapped in such tissue paper. The absorbent core is a mixture of cellulose fiber, fluffed and airlaid with super absorbent polymer (SAP) available from commercial sources. The basis weight is about 500-700 $g/m^2$. There is a moisture proof polymer backsheet 16 below the core of 0.5 mil. Wet laid sheets may also be used.

The above described examples, embodiments, and comparisons are intended to illustrate the various aspects of the invention without limitation of same but the appended claims and elements thereof including reasonable equivalents for these are to define the metes and bounds of the Invention.

What is claimed:

1. A method for making an absorbent composite useful for personal hygiene articles comprising: treating a wood fiber pulp with an alkali solution at a temperature below 60° C. and thereby forming an alkali-treated fiber wood pulp; drying and fluffing the alkali-treated wood fiber pulp to form an absorbent sublayer material which is without chemical crosslinking; providing at least one fluid permeable topsheet layer and at least one substantially fluid impermeable backsheet layer; and interposing the sublayer material between the topsheet layer and the backsheet layer.

2. The method of claim 1 wherein the wood fiber pulp is treated with an alkali solution having a concentration of about 5% to about 25% by weight in a suspension in which the wood fiber pulp is about 2% to about 25% by weight, and said treatment temperature is below about 50° C.

3. The method of claim 2 wherein the alkali solution has concentration of about 6% to about 18% by weight, said suspension is about 2% to about 10% by weight wood fiber pulp, and said treatment temperature is below about 40° C.

4. The method of claim 3 wherein the alkali solution has a concentration of about 13% to about 18% by weight, said suspension is about 3% to about 8% by weight wood fiber pulp, and said treatment temperature is below about 40° C.

5. The method of claim 4 wherein said treatment is at a temperature is below about 35° C.

6. The method of claim 5 wherein said alkali-treated wood fiber pulp is blended with a wood fiber pulp which is not alkali-treated and a sublayer material containing about 25% to about 100% by weight alkali-treated wood fiber pulp is formed.

7. The method of claim 3 wherein said treatment temperature is below about 35° C.

8. The method of claim 3 wherein said alkali-treated wood fiber pulp is blended with a wood fiber pulp which is not alkali-treated and a sublayer material containing about 25% to about 100% by weight alkali-treated wood fiber pulp is formed.

9. The method of claim 2 wherein said alkali-treated wood fiber pulp is blended with a wood fiber pulp which is not alkali-treated and a sublayer material containing about 25% to about 100% by weight alkali-treated wood fiber pulp is formed.

10. The method of claim 1 wherein said alkali-treated wood fiber pulp is blended with a wood fiber pulp which is not alkali-treated and a sublayer material containing about 25% to about 100% by weight alkali-treated wood fiber pulp is formed.

11. A method for making an absorbent composite useful for personal hygiene articles comprising:
    (a) creating a suspension of about 2% to about 25% by weight of a cellulosic fiber pulp in an alkali solution having an alkali concentration from about 2% to about 25% by weight and a temperature below about 50° C.;
    (b) maintaining said cellulosic fiber pulp in said suspension for a treatment time between about 2 to about 10 minutes to obtain an alkali extracted cellulosic fiber pulp having improved absorbency characteristics;
    (c) recovering said alkali extracted cellulosic fiber pulp from said suspension;
    (d) drying said alkali extracted cellulosic fiber pulp;
    (e) fluffing said alkali extracted cellulosic fiber pulp;
    (f) forming an absorbent layer from said alkali extracted cellulosic fiber pulp without chemical crosslinking thereof;
    (g) providing at least one fluid permeable layer; and
    (h) incorporating said absorbent layer into an absorbent structure wherein the absorbent layer is at least partially covered by said fluid permeable layer.

12. The method of claim 11 wherein said suspension is about 2% to about 10% by weight of a cellulosic fiber pulp, has an alkali concentration from about 6% to about 18% and a temperature below 40° C.

13. The method of claim 12 wherein the temperature of said suspension is below about 35° C.

14. The method of claim 13 wherein said alkali extracted cellulosic fiber pulp is blended with a cellulosic fiber pulp which is not alkali extracted and an absorbent layer containing about 25% to 100% by weight alkali extracted cellulosic fiber pulp is formed.

15. The method of claim 12 wherein said alkali extracted cellulosic fiber pulp is blended with a cellulosic fiber pulp which is not alkali extracted and an absorbent layer containing about 25% to 100% by weight alkali extracted cellulosic fiber pulp is formed.

16. The method of claim 11 wherein said suspension is about 3% to about 8% by weight of a cellulosic fiber pulp, has an alkali concentration from about 13% to about 18% and a temperature below 40° C.

17. The method of claim 16 wherein the temperature of said suspension is below about 35° C.

18. The method of claim 16 wherein said alkali extracted cellulosic fiber pulp is blended with a cellulosic fiber pulp which is not alkali extracted and an absorbent layer containing about 25% to 100% by weight alkali extracted cellulosic fiber pulp is formed.

19. The method of claim 11 wherein said alkali extracted cellulosic fiber pulp is blended with a cellulosic fiber pulp which is not alkali extracted and an absorbent layer containing about 25% to 100% by weight alkali extracted cellulosic fiber pulp is formed.

* * * * *